United States Patent
Plutzky et al.

(10) Patent No.: US 9,504,660 B2
(45) Date of Patent: Nov. 29, 2016

(54) RETINALDEHYDE MIMETICS AND INHIBITORS OF RETINALDEHYDE DEHYDROGENASE I IN THE TREATMENT OF DISORDERS

(71) Applicant: THE BRIGHAM AND WOMEN'S HOSPITAL, INC., Boston, MA (US)

(72) Inventors: Jorge Plutzky, Chestnut Hill, MA (US); Florian Kiefer, Vienna (AT)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/376,209

(22) PCT Filed: Feb. 1, 2013

(86) PCT No.: PCT/US2013/024439
§ 371 (c)(1),
(2) Date: Aug. 1, 2014

(87) PCT Pub. No.: WO2013/116721
PCT Pub. Date: Aug. 8, 2013

(65) Prior Publication Data
US 2014/0378530 A1    Dec. 25, 2014

Related U.S. Application Data

(60) Provisional application No. 61/594,841, filed on Feb. 3, 2012, provisional application No. 61/642,815, filed on May 4, 2012.

(51) Int. Cl.
| | | |
|---|---|---|
| C07H 21/02 | (2006.01) |
| C07H 21/04 | (2006.01) |
| C12N 15/11 | (2006.01) |
| A61K 48/00 | (2006.01) |
| A61K 31/11 | (2006.01) |
| A61K 31/145 | (2006.01) |
| A61K 31/4164 | (2006.01) |
| A61K 31/7105 | (2006.01) |
| C12N 15/113 | (2010.01) |

(52) U.S. Cl.
CPC .............. *A61K 31/11* (2013.01); *A61K 31/145* (2013.01); *A61K 31/4164* (2013.01); *A61K 31/7105* (2013.01); *C12N 15/1137* (2013.01); *C12N 2310/14* (2013.01); *C12N 2320/30* (2013.01); *C12N 2320/31* (2013.01)

(58) Field of Classification Search
USPC ........................................... 514/44, 2
See application file for complete search history.

(56) References Cited

U.S. PATENT DOCUMENTS

2011/0046234 A1    2/2011 Plutzky et al.

FOREIGN PATENT DOCUMENTS

| EP | 2077327 | 7/2009 |
| KR | 100878586 | 1/2009 |
| WO | 2010066852 | 6/2010 |

OTHER PUBLICATIONS

Database GenBank: BC035322.1, Mar. 1, 2008.
(Continued)

*Primary Examiner* — Terra C Gibbs
(74) *Attorney, Agent, or Firm* — Nixon Peabody LLP

(57) ABSTRACT

The technology described herein is directed to methods of treating, e.g. obesity by administering retinaldehyde increasing agents.

19 Claims, 9 Drawing Sheets

(56) References Cited

OTHER PUBLICATIONS

Moreb, J. S. et al., "RNAi-Mediated Knockdown of Aldehyde Dehydrogenase Class-1A1 and Class-3A1 is Specific and Reveals that Each Contributes Equally to the Resistance Against 4-Hydroperoxycyclophosphamide," Cancer Chemotherapy and Pharmacology, vol. 59, No. 1, 2007, pp. 127-136.

Russo, J. et al., "Identification of 4-(N, N-Dipropylamino) Benzaldehyde as a Potent, Reversible Inhibitor of Mouse and Human Class I Aldehyde Dehydrogenase," Biochemical Pharmacology, vol. 50, No. 3, 1995, pp. 399-406.

Ziouzenkova, O. et al., "Retinaldehyde Represses Adipogenesis and Diet-Induced Obesity." Nature Medicine, vol. 13, No. 6, 2007, pp. 695-702.

Schwarz et al., Mol Cell Biol 17:1552-1561 (1997). "Retinoic acid blocks adipogenesis by inhibiting C/EBPbeta-mediated transcription."

Kane et al., Molecular and Cellular Biology 31(16):3277-3285 (2010). "Crbpl modulates glucose homeostasis and pancreas 9-cis-reinoic acid concentrations."

Altucci et al., NatRev Drug Discovery 6:793-810 (2007). "RAR and RXR modulation in cnacer and metabolic disease."

Villarroya et al., Current Medicinal Chem 11:795-805 (2004). "Retinoids and retinoid receptors in the control of energy balance: novel pharmacological strategies in obesity and diabetes."

Klein et al., Diabetes Care 30(6):1647-1652 (2007). "Waist circumference and cardiometbaloic risk."

Koppaka et al., Pharmacological Reviews 64:520-539 (2012). "Aldehyde dehydrogenase inhibitors: a comprehensive review of the pharmacology, mechanism of action, substrate specificity, and clinical application."

Ziouzenkova et al. FEBS Letters 582:32-38 (2007) "Retinoid metabolism and nuclear receptor responses:New insights into coordinated regulation of the PPAR-RXR complex".

Reichert et al. Molecular Endocrinology 25:799-809 (2011) "Concerted Action of Aledhyde Dehydrogenases Influences Depot-Specific Fat Formation."

Vrieze et al., Diabetologia 54:S15-S16 (2011) "New insulin sensitizers produce differentiation of brown-like adipose cells from a subcutanous fat depot and increase secretin of adiponectin in vitro."

Al Qatari et al., British Journal of Pharmacology 110:67P (1993) "Effect of aldehyde dehydrogenase inhibitors on brown adipose tissue ethanol metabolism and lipogenesis in CBA mice."

Aldh controls endogenous Rald levels

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aacacgacta tgctggttac                                                    20

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 3
<211> LENGTH: 2378
<212> TYPE: DNA
<213> ORGANISM: Homo sapiens

<400> SEQUENCE: 3
gctgcataca cttatcacag gtttcggctt tgtaaattaa ttcatctgca aatagtgcac        60
tgtctccagg tacaaattcg atgctggagc actggtttct taaggattta agtttaaagt       120
caaaggcttc ctgccctagg tgttacaaat aagtagtgtc gttttctttt tttgctctga       180
gtttgttcat ccaatcgtat ccgagtatgc aaataaactt tagcccgtgc agataaaaaa       240
ggaacaaata aagccaagtg ctctatcaga accaaattgc tgagccagtc acctgtgttc       300
caggagccga atcagaaatg tcatcctcag gcacgccaga cttacctgtc ctactccacg       360
atttgaagat tcaatatact aagatcttca taaacaatga atggcatgat tcagtgagtg       420
gcaagaaatt tcctgtcttt aatcctgcaa ctgaggagga gctctgccag gtagaagaag       480
gagataagga ggatgttgac aaggcagtga aggccgcaag acaggctttt cagattggat       540
ccccgtggcg tactatggat gcttccgaga ggggcgact attatacaag ttggctgatt       600
taatcgaaag agatcgtctg ctgctggcga caatggagtc aatgaatggt ggaaaactct       660
attccaatgc atatctgaat gatttagcag gctgcatcaa acattgcgc tactgtgcag        720 gttgggctga caagatccag ggccgtacaa taccaattga tggaaatttt tttacatata       780
caagacatga acctattggt gtatgtggcc aaatcattcc ttggaatttc ccgttggtta       840
tgctcatttg gaagataggg cctgcactga gctgtgaaaa cacagtggtt gtcaaaccag       900
cagagcaaac tcctctcact gctctccacg tggcatcttt aataaaagag gcagggtttc       960
ctcctggagt agtgaatatt gttcctggtt atgggcctac agcaggggca gcatttctt      1020 ctcacatgga tatagacaaa gtagccttca caggatcaac agaggttggc aagttgatca      1080
aagaagctgc cggaaaaagc aatctgaaga gggtgaccct ggagcttgga ggaaagagcc      1140
cttgcattgt gttagctgat gccgacttgg acaatgctgt tgaatttgca caccatgggg      1200

```
tattctacca ccagggccag tgttgtatag ccgcatccag gattttttgtg gaagaatcaa    1260 tttatgatga gtttgttcga aggagtgttg agcgggctaa gaagtatatc cttggaaatc    1320
ctctgacccc aggagtcact caaggccctc agattgacaa ggaacaatat gataaaatac    1380
ttgacctcat tgagagtggg aagaaagaag gggccaaact ggaatgtgga ggaggcccgt    1440
gggggaataa aggctacttt gtccagccca cagtgttctc taatgttaca gatgagatgc    1500
gcattgccaa agaggagatt tttggaccag tgcagcaaat catgaagttt aaatctttag    1560
atgacgtgat caaaagagca acaatactt tctatggctt atcagcagga gtgtttacca    1620
aagacattga taaagccata acaatctcct ctgctctgca ggcaggaaca gtgtgggtga    1680
attgctatgg cgtggtaagt gcccagtgcc cctttggtgg attcaagatg tctggaaatg    1740
gaagagaact gggagagtac ggtttccatg aatatacaga ggtcaaaaca gtcacagtga    1800
aaatctctca gaagaactca taaagaaaat acaagagtgg agagaagctc ttcaatagct    1860
aagcatctcc ttacagtcac taatatagta gattttaaag acaaaatttt tcttttcttg    1920 attttttaa acataagcta atcatatta gtattaatac tacccataga aaacttgaca    1980
tgtagcttct tctgaaagaa ttatttgcct tctgaaatgt gaccccccaag tcctatccta    2040 aataaaaaaa gacaaattcg gatgtatgat ctctctagct ttgtcatagt tatgtgattt    2100
tcctttgtag ctacttttgc aggataataa ttttatagaa aaggaacagt tgcatttagc    2160
ttctttccct tagtgactct tgaagtactt aacatacacg ttaactgcag agtaaattgc    2220
tctgttccca gtagttataa agtccttgga ctgttttgaa aagtttccta ggatgtcatg    2280
tctgcttgtc aaaagaaata atccctgtaa tatttagctg taaactgaat ataaagctta    2340
ataaaaacaa ccttgcatga ttcttgttaa aaaaaaaa                            2378
```

<210> SEQ ID NO 4
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Ser Ser Gly Thr Pro Asp Leu Pro Val Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160

Gly Val Cys Gly Gln Ile Ile Pro Trp Asn Phe Pro Leu Val Met Leu
            165                 170                 175

Ile Trp Lys Ile Gly Pro Ala Leu Ser Cys Gly Asn Thr Val Val
        180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
            275                 280                 285

Glu Phe Ala His His Gly Val Phe Tyr His Gln Gly Gln Cys Cys Ile
290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
            355                 360                 365

Glu Cys Gly Gly Gly Pro Trp Gly Asn Lys Gly Tyr Phe Val Gln Pro
370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
            435                 440                 445

Ala Gly Thr Val Trp Val Asn Cys Tyr Gly Val Val Ser Ala Gln Cys
450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Leu Glu Ala Leu Ala Glu Ala Leu Glu Ala Leu Ala Glu Ala
1               5                   10                  15

<210> SEQ ID NO 7
<211> LENGTH: 16
<212> TYPE: PRT
<213> ORGANISM: Unknown
<220> FEATURE:
<223> OTHER INFORMATION: Description of Unknown: Exemplary hydrophobic
      membrane translocation containing peptide

<400> SEQUENCE: 7

Ala Ala Val Ala Leu Leu Pro Ala Val Leu Leu Ala Leu Leu Ala Pro
1               5                   10                  15

<210> SEQ ID NO 8
<211> LENGTH: 11
<212> TYPE: PRT
<213> ORGANISM: Unknown
<220> FEATURE:
<223> OTHER INFORMATION: Description of Unknown: RFGF
      analogue peptide

<400> SEQUENCE: 8

Ala Ala Leu Leu Pro Val Leu Leu Ala Ala Pro
1               5                   10

<210> SEQ ID NO 9
<211> LENGTH: 13
<212> TYPE: PRT
<213> ORGANISM: Human immunodeficiency virus

<400> SEQUENCE: 9

Gly Arg Lys Lys Arg Arg Gln Arg Arg Arg Pro Pro Gln
1               5                   10

<210> SEQ ID NO 10
<211> LENGTH: 16
<212> TYPE: PRT
<213> ORGANISM: Drosophila sp.

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 11
cgtggcgtac tatggatgc                                              19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcagcagacg atctctttcg                                             20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccatggatgc ttcagagagg                                             20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actttcccac cattgagtgc                                             20
```

RETINALDEHYDE MIMETICS AND INHIBITORS OF RETINALDEHYDE DEHYDROGENASE I IN THE TREATMENT OF DISORDERS

CROSS REFERENCE TO RELATED APPLICATIONS

This Application is a 35 U.S.C. 371 National Phase Entry Application of International Application No. PCT/US2013/024439 filed Feb. 1, 2013, which designates the U.S., and which claims the benefit under 35 U.S.C. §119(e) of U.S. Provisional Application No. 61/594,841, filed Feb. 3, 2012, and 61/642,815 filed May 4, 2012, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 1, 2013, is named 043214PC.txt and is 11,108 bytes in size.

TECHNICAL FIELD

The technology described herein relates to the treatment of disorders, e.g. obesity, by administering retinaldehyde increasing agents.

BACKGROUND

While obesity is well known as a risk factor for metabolic diseases (e.g. diabetes), visceral white fat (i.e. visceral white adipose tissue or visceral WAT) is particularly associated with disease risk (Klein, S., et al. Diabetes care 30, 1647-1652 (2007)). In contrast, brown adipose tissue (BAT) can be beneficial to a subject and increasing BAT formation has been explored as a therapeutic approach to treating metabolic disorders and obesity.

SUMMARY

As described herein, the inventors have discovered that retinaldehyde (Rald) promotes brown adipose tissue (BAT) phenotypes such as thermogenesis and UCP-1 gene expression. The enzyme Aldh1a1 catalyzes the conversion of Rald to retinoic acid (See, e.g. FIG. 7) and therefore suppresses these BAT phenotypes. Increased levels of Rald, e.g. by inhibiting Aldh1a1 and/or increasing Rald levels (e.g. adding exogenous Rald) are demonstrated herein to cause white adipose tissue to assume a more BAT-like phenotype, leading to, e.g. a decrease in BMI, increase in core body temperature, and an increase in markers of metabolic health such as glucose and insulin tolerance. Accordingly, described herein are methods of administering retinaldhyde increasing agents for the treatment of certain conditions, e.g. obesity and/or metabolic disorder.

In one aspect, described herein is a method of inducing a brown adipose tissue (BAT)-like phenotype in a white adipose tissue (WAT) of a subject; the method comprising administering a therapeutically effective amount of a retinaldehyde increasing agent to the subject. In some embodiments, the BAT-like phenotype can comprise an increase in a parameter selected from the group consisting of: RAR expression; RAR activity; UCP-1 expression; thermogenesis; and uncoupled mitochondrial respiration. In some embodiments, the WAT can be visceral WAT. In some embodiments, the subject can be a subject in need of a reduction of white adipose tissue. In some embodiments, the subject can be a subject in need of treatment for a metabolic disorder. In some embodiments, the metabolic disorder can be selected from the group consisting of: obesity; excess adipose tissue; diabetes; and cardiovascular disease. In some embodiments, the subject with obesity can have a body mass index of at least about 25 kg/m$^2$ prior to administration. In some embodiments, the subject with obesity can have a body mass index of at least about 30 kg/m$^2$ prior to administration. In some embodiments, the subject can be a subject selected from the group consisting of: a subject in need of an increased body temperature; a subject in need of treatment or prevention of exposure to low temperatures; and a subject in need of treatment or prevention of hypothermia.

In one aspect, described herein is a method for inducing weight loss in a subject, the method comprising, administering a therapeutically effective amount of a retinaldehyde increasing agent to the subject; wherein a therapeutically effective amount of a retinaldehyde increasing agent is an amount sufficient to induce a BAT-like phenotype in WAT cells.

In one aspect, described herein is the use of a retinaldehyde increasing agent to induce a brown adipose tissue (BAT)-like henotype in a white adipose tissue (WAT) of a subject; wherein a therapeutically effective amount of a retinaldehyde increasing agent is administered to the subject. In some embodiments, the BAT-like phenotype can comprise an increase in a parameter selected from the group consisting of: RAR expression; RAR activity; UCP-1 expression; thermogenesis; and uncoupled mitochondrial respiration. In some embodiments, the WAT can be visceral WAT. In some embodiments, the subject can be a subject in need of a reduction of white adipose tissue. In some embodiments, the subject can be a subject in need of treatment for a metabolic disorder. In some embodiments, the metabolic disorder can be selected from the group consisting of: obesity; excess adipose tissue; diabetes; and cardiovascular disease. In some embodiments, the subject with obesity can have a body mass index of at least about 25 kg/m$^2$ prior to administration. In some embodiments, the subject with obesity can have a body mass index of at least about 30 kg/m$^2$ prior to administration. In some embodiments, the subject can be a subject selected from the group consisting of: a subject in need of an increased body temperature; a subject in need of treatment or prevention of exposure to low temperatures; and a subject in need of treatment or prevention of hypothermia.

In one aspect, described herein is the use of a retinaldehyde increasing agent for inducing weight loss in a subject, wherein a therapeutically effective amount of a retinaldehyde increasing agent is administered to the subject; and wherein a therapeutically effective amount of a retinaldehyde increasing agent is an amount sufficient to induce a BAT-like phenotype in WAT cells.

In some embodiments of any of the foregoing aspects, the therapeutically effective amount of a retinaldehyde increasing agent does not substantially reduce lean body mass of the subject. In some embodiments of any of the foregoing aspects, the retinaldehyde increasing agent can be retinaldehyde. In some embodiments of any of the foregoing aspects, the retinaldehyde increasing agent can be an inhibitor of Aldh1a1. In some embodiments of any of the foregoing aspects, the inhibitor of Aldh1a1 can be an inhibitory nucleic acid. In some embodiments of any of the foregoing aspects, the inhibitory nucleic acid can comprise the sequence of SEQ ID NO:1 or a variant thereof. In some embodiments of any of the foregoing aspects, the inhibitor of Aldh1a1 can be a small molecule inhibitor. In some embodiments of any of the foregoing aspects, the inhibitor can be selected from the group consisting of: diethyl aminobenzaldehyde (DEAB); citral; 4-(n,n-dipropylamino)benzaldehyde (DPAB); ampal; disulfiram; S-methyl-N,N-diethylthiocarbamate sulfoxide (DETC-MeSO); coprine; cyanamide daidzin; 1-aminocyclopropanol (ACP), cephalosporins, gossypol; isosorbide esters; metronidazole; or metabolites or analogs of any of the foregoing exhibiting ALDH1-inhibiting activity. In some embodiments of any of the foregoing aspects, both retinaldehyde and an inhibitor of Aldh1a1 can be administered.

In some embodiments of any of the foregoing aspects, the administration can be local. In some embodiments of any of the foregoing aspects, the administration can be systemic. In some embodiments of any of the foregoing aspects, the administration can be selected from the group consisting of: intraperitoneal; oral; and intravenous. In some embodiments of any of the foregoing aspects, the subject can be human. In some embodiments of any of the foregoing aspects, the subject can be a companion animal. In some embodiments of any of the foregoing aspects, the subject can be a dog or cat.

BRIEF DESCRIPTION OF THE DRAWINGS

FIG. 1A depicts a graph of Aldh1a1 mRNA and protein expression in different fat depots of female C57131/6.3 mice (n=10). FIG. 1B depicts a graph of Aldh1a1 mRNA and protein expression in visceral (visc AT) and subcutaneous (sc AT) adipose tissue from non-obese male and female subjects (n=20). FIG. 1C depicts a graph of Aldh1a1 mRNA and protein expression in GWAT from standard chow-fed (SC) lean and high fat-fed (HF) obese C57131/6J mice (n=8/group). FIG. 1D depicts a graph of Aldh1a1 mRNA and protein expression in visceral adipose tissue from non-obese (BMI25.2±0.15 kg/m$^2$) and morbidly obese subjects (BMI53.0±0.55 kg/m$^2$; n=20/group). Representative western blots are shown. FIG. 1E depicts a graph of Linear regression analysis between BMI and Aldh1a1 mRNA expression in human visceral adipose tissue (n=40), **p<0.01, mp<0.001.

FIG. 2A depicts a graph of UCP-1 mRNA expression in GWAT, SWAT and BAT of standard chow-fed WT and Aldh1a1$^{4-}$ mice. FIG. 2B depicts graphs of mRNA expression of classic brown fat markers in GWAT, SWAT and BAT of WT versus Aldh1a1$^{4-}$ mice. FIG. 2C depicts a graph of mitochondrial DNA content (genomic ND1 expression) was determined in GWAT, SWAT and BAT of WT versus Aldh1a1$^{-}$ mice. n=6-8/group, *p<0.05, "p<0.01, ***p<0.001.

FIGS. 3A-3B depicts graphs of citrate synthase activity (FIG. 3A) and oxygen consumption rate (FIG. 3B) in GWAT and BAT of WI versus Aldh1a1$^{4}$ mice as measured by enzymatic assays and Seahorse Extracellular Flux Analyzer, respectively. FIG. 3C depicts a graph of core body temperature of WT versus Aldh1a1$^{-/-}$ mice. Results represent average body temperature over a 48 h period at 23° C. and 4° C., respectively. FIG. 3D depicts a representative UCP-1 western blot in GWAT, SWAT and BAT of WT versus Aldh1a1$^{4-}$ mice after 48 h of cold stimulation. n=6-8/group, *p<0.05.

FIG. 4A depicts a graph of UCP1 mRNA expression levels in 10T1/2 cells after adipocyte differentiation in the presence or absence of the Aldh inhibitor DEAB (1 pM). FIG. 4B depicts a graph of UCP-1 mRNA analysis in 10T1/2 cells that were stably transfected with scrambled (shCtrl) or Aldh1a1-targeting (shAldh1a1) shRNA prior to adipocyte differentiation and mRNA analysis. FIGS. 4C-4D depicts graphs of 10T1/2 cells (FIG. 4C) and human stromal-vascular cells (FIG. 4D) isolated from subcutaneous fat biopsies were differentiated into adipoyctes in the presence or absence of Rald (1 pM) followed by quantification of UCP-1 gene expression. FIG. 4E depicts a graph of gene expression. 10T1/2 cells were stimulated with 1 pM DEAB, 1 pM Raid or both during differentiation and UCP-1 gene expression was measured. FIGS. 4F-4G depict graphs of UCP-1 expression in shAldh1a1-transfected 10T1/2 cells (FIG. 4F) and mouse embryonic fibroblasts (MEFs) (FIG. 4G) isolated from Aldh1a1-deficient embryos stimulated with Raid (1 pM) during adipogenic differentiation followed by UCP-1 mRNA analysis. n=5-6/condition, *p<0.05, "p<0.01, ***p<0.001.

FIG. 5A depicts a graph of UCP-1 mRNA expression in 10T1/2 adipocytes stimulated with either the RAR antagonist AGN193109 (AGN), the RXR antagonist HX531, Rald (1 pM) or the combination of Raid/AGN or Raid/HX531 (each 1 pM) during adipogenic differentiation. FIG. 5B depicts a graph of UCP-1 mRNA expression in 10T1/2 cells transfected with scrambled (siCtrl) or RARa siRNA (siRARa) and differentiated in the presence of Raid (1 pM) followed by UCP-1 mRNA quantification. FIG. 1C depicts a graph of UCP-1 gene expression in shControl and shAldh1a1-transfected 10T1/2 cells stimulated with AGN193109 or HX531 (both 1 pM) during adipogenic differentiation followed by UCP-1 mRNA quantification. FIG. 5D depicts a graph of UCP-1 gene expression in 10T1/2 cells with stable Aldh1a1 knockdown (shAldh1a1) transfected with siCtri or siRARα followed by adipocyte differentiation and UCP-1 mRNA analysis. FIGS. 5E-5F depict graphs of cell-free TR-FRET assays performed to assess ligand-dependent recruitment of PGC-1a to either the (FIG. 5E) RARa- or (FIG. 5F) RXRa-LBD, respectively. Dose response curves for Raid, ATRA, and 9cisRA are shown. FIG. 5G depicts a graph of luciferase activity in undifferentiated 10T1/2 cells, which lack Aldhs, transfected with an RARE-luciferase construct (RARE-Luc) followed by stimulation (24 h) with increasing concentrations of Raid or ATRA. FIGS. 5H-5I depict graphs of luciferase activity in undifferentiated 10T1/2 cells transfected with a murine 3.1 kb UCP-1 promoter luciferase construct (UCP1-Luc) and subsequently stimulated (24 h) with (FIG. 5H) cAMP (250 pM), Raid (1 pM), Retinol (1 pM) or (FIG. 5I) increasing concentrations of Raid. Normalized luciferase activities are shown as fold change. FIG. 5J depicts graphs of RAR-α and PGC-1α enrichment and electrophoresis results of 10T1/2 cells which have undergone adipocyte differentiation in the presence or absence of Raid (1 pM). RARa and PGC-1a recruitment to the UCP-1 promoter region was determined by ChIP. Fold enrichment and a representative DNA gel pictures are given. n=5-6/condition, "p<0.01, ***p<0.001; Veh=vehicle.

FIGS. 6A-6B depict a graph of Aldh1a1 mRNA expression (FIG. 6A) and an image of Aldh1a1 mRNA protein expression in indicated tissues of Aldh1a1 and Ctrl ASO mice; (Ctrl=Ctrl ASO, ASO=Aldh1a1 ASO). FIGS. 6C-6D depict a graph of UCP-1 mRNA expression (FIG. 6C) and an image of UCP-1 protein expression in GWAT, SWAT and BAT of Aldh1a1 versus Ctrl ASO treated mice. FIG. 6E depicts a graph of core body temperature of Aldh1a1 versus Ctrl ASO-treated mice at 23° C. and at 4° C. over 48 h (n=6/group). FIGS. 6F-6I depict graphs of results from a cohort of C57Bl/6i mice (n=16) was fed a high-fat diet (HFD) for 8 weeks prior to initiation of Aldh1a1 or Ctrl ASO treatment (n=8/group), continued HFD, and measurement of (FIGS. 6F-6G) body weight gain, (FIG. 6H) fat depots mass, and (FIG. 6I) insulin tolerance testing (at 17 weeks). *$p<0.05$, "$p<0.01$, ***$p<0.001$.

DETAILED DESCRIPTION

Figures 1A, 1B, 1C, 1D, 1E:
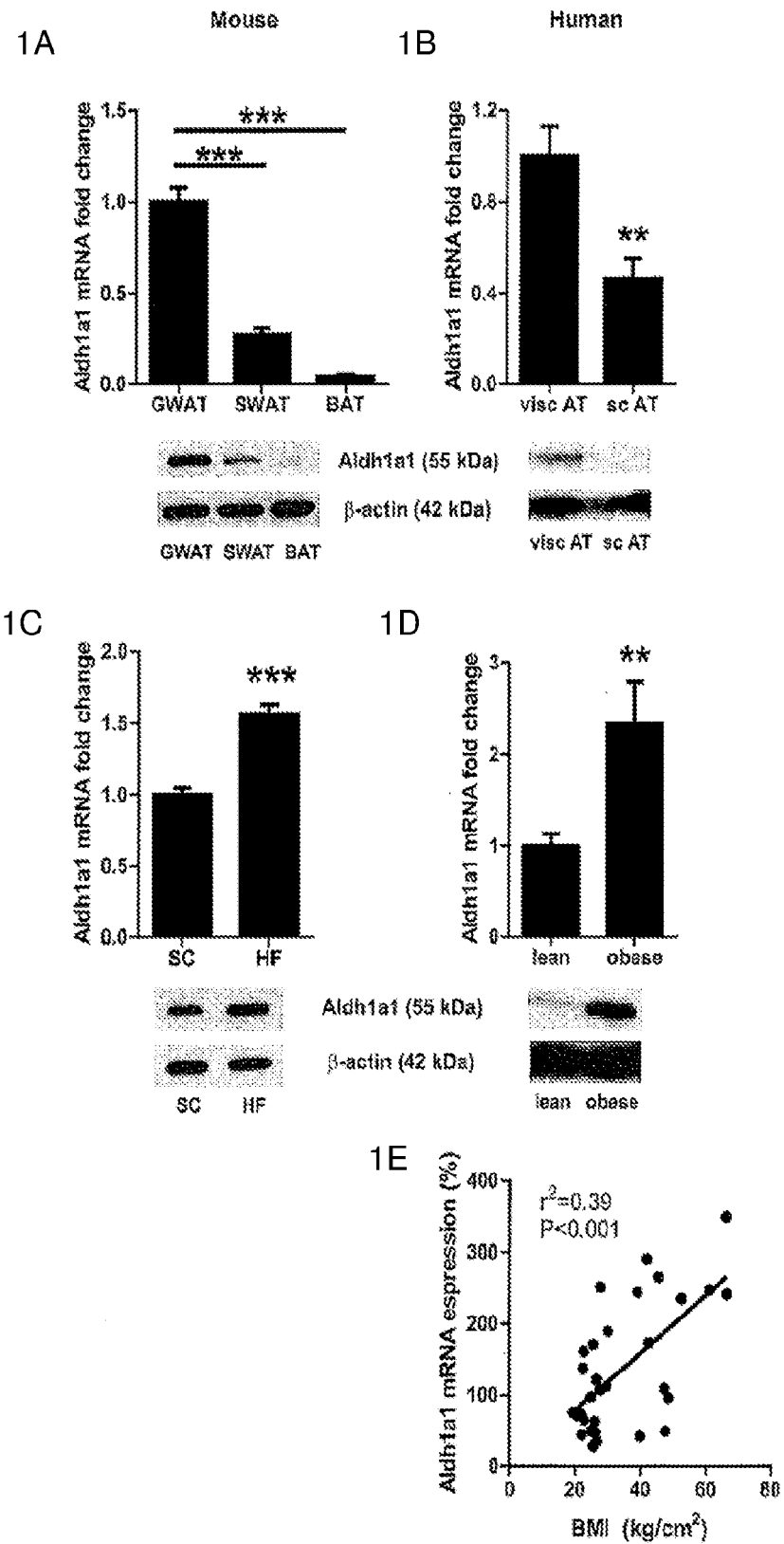
FIGS. 1A-1E demonstrate that Aldh1a1 is present primarily in visceral fat and its expression correlates with obesity.

As described herein, the inventors have found that the level of retinaldehyde present in an adipocyte can modulate the phenotype of the cell. Specifically, increased levels of retinaldehyde cause white adipocytes to assume a phenotype which more closely resembles that of a brown adipocyte, e.g. engaging in themogenesis, expressing UCP-1, etc. Accordingly, in one aspect, described herein is a method of inducing a brown adipose tissue (BAT)-like phenotype in a white adipose tissue (WAT) of a subject; the method comprising administering a therapeutically effective amount of a retinaldehyde increasing agent to the subject. In some embodiments, the Aldh1a1 enzyme is inhibited, e.g. to reduce the rate of conversion of Rald to retinoic acid. In some embodiments, the level of Rald is increased, e.g. by inhibiting Aldh1a1 and/or adding exogenous Rald. In some embodiments, Aldh1a1 expression and/or activity is decreased and the level of Rald is increased, e.g. by inhibiting Aldh1a1 and/or adding exogenous Rald or precursors thereof.

The term "adipose tissue" refers to loose connective tissue which stores fat and is composed of multiple cell types, including adipocytes and microvascular cells. Adipose tissue also comprises stem and progenitor cells and endothelial precursor cells. Two varieties of adipose tissue are found in mammals; white adipose tissue and brown adipose tissue.

As the name would imply, white adipose tissue (WAT) comprises white adipocytes, which are adipocytes comprising a single large fat droplet, with a flattened nucleus located on the periphery of the cell. White adipose tissue functions to help maintain body temperature (via insulation) and to store energy in the form of lipids. In addition to morphology, WAT can be distinguished by the expression of marker genes, which are well known and include, by way of non-limiting example, lipoprotein lipase (LPL; NCBI Gene ID No. 4023), hormone-sensitive lipase (HSL; NCBI Gene ID No. 3991), adiponectin (ADIPOQ NCBI Gene ID No. 9370), FABP4 (NCBI Gene ID No. 2167), CEBPA (NCBI Gene ID No. 1050), and PPARG2 (NCBI Gene ID No. 5468). WAT can be further characterized as visceral WAT (also know as abdominal fat, organ fat, or intra-abdominal fat) or subcutaneous fat. Visceral fat is located in the abdominal cavity, typically between the organs (e.g. stomach, liver, kidneys, etc.) An excess amount of visceral WAT comprises a condition referred to as central obesity and is linked to type 2 diabetes, insulin resistance, inflammatory disease, and additional obesity-related conditions. In some embodiments, WAT can be visceral WAT. Subcutaneous fat is found in the hypodermis just below the skin.

In contrast to WAT, brown adipose tissue (BAT) comprises brown adipose cells that utilize the chemical energy in lipids and glucose to produce heat via non-shivering thermogenesis[12]. Brown adipose cells comprise multiple lipid droplets throughout the cell, a rounded nucleus and a large number of mitochondria, which give the cells their distinctive brown color. Marker genes of brown adipocytes are well known and include, by way of non-limiting example, lipoprotein lipase (LPL), UCP1 (NCBI Gene ID No. 7350), ELOVL3 (NCBI Gene ID No. 83401), PGC1A (NCBI Gene ID No. 10891), CYC1 (NCBI Gene ID No. 1537), CEBPA, PPARG2, CYCS (NCBI Gene ID No. 54205), PRDM16 (NCBI Gene ID No. 63976), CIDEA (NCBI Gene ID No. 1149), COX4 (NCBI Gene ID No. 1327), TFAM (NCBI Gene ID No. 7019), and NRF1 (NCBI Gene ID No. 4899). Brown adipocytes can be distinguished from white adipocytes by having high relative expression of, by way of non-limiting example, UCP1, ELOVL3, PGC1A, and CYC1 and low relative expression of, by way of non-limiting example, ADIPOO, HSL, and FABP4, while both cell types will display high levels of PPARγ2 and LPL expression. Brown adipocytes are also characterized by RAR expression, RAR activity, UCP-1 expression, thermogenesis, and uncoupled mitochondrial respiration.

A number of markers, characteristics, and/or parameters of BAT are described herein, particularly those that distinguish it from WAT. As used herein, a "brown adipose tissue-like" or "BAT-like" phenotype refers to a phenotype in which a cell (or tissue) displays a level of at least one marker, characteristic and/or parameter which differs between BAT and WAT such that the level of the marker, characteristic and/or parameter deviates (in a statistically significant amount) from the level of that marker and/or parameter in a WAT reference level so that the cell (or tissue) more closely resembles BAT than does the WAT reference level for at least one marker, characteristic, and/or parameter. For example, a WAT cell which is treated according to the methods described herein and which thereafter displays a statistically significant increase in thermogenesis as compared to a WAT reference level is a cell which has been modulated to display a BAT-like phenotype. In some embodiments, the statistically significant amount is a change of at least 10% relative to the WAT reference level, e.g. 10% or more, 20% or more, 30% or more, 40% or more, 50% or more, 60% or more, 70% or more, 80% or more, 90% or more, 100% or more relative to the WAT control. As used herein, "WAT reference level" refers to a level and/or amount of a marker, characteristic, and/or parameter in a WAT cell and/or tissue which has not been treated according to the methods described herein. In some embodiments, the WAT reference level of a marker can be the level of the marker in a WAT cell and/or tissue. In some embodiments, the WAT reference level can be the level in a sample of similar cell type, sample type, sample processing, and/or obtained from a subject of similar age, sex and other demographic parameters as the cell and/or tissue which is to be treated according to the methods described herein. Accordingly, in some embodiments, the WAT reference level of a BAT-like phenotype marker can vary as demographic factors such as age, gender, genotype, environmental factors, and individual medical histories vary.

In some embodiments, an a BAT-like phenotype can comprise an increase in a parameter selected from the group consisting of RAR expression; RAR activity; UCP-1 expression; thermogenesis; and uncoupled mitochondrial respiration, as compared to an untreated WAT reference level. In some embodiments, an increase in a BAT-like phenotype can comprise an increase in a parameter selected from the group consisting of RAR expression; RAR activity; UCP-1 expression; thermogenesis; and uncoupled mitochondrial respiration.

As used herein, a "retinaldehyde increasing agent" refers to any agent which can cause an increase in the concentration of retinaldehyde in a cell. In some embodiments, the cell is a white adipocyte. An increased concentration of retinaldehyde can be the result of, for example, an increase the level and/or activity of a polypeptide that promotes the synthesis and/or biogenesis of retinaldehyde or a decrease in the level and/or activity of a polypeptide that promotes the degradation and/or conversion of retinaldehyde to other compounds, e.g. retinoic acid. The term "agent" refers generally to any entity which is normally not present or not present at the levels being administered to a cell, tissue or subject. An agent can be selected from a group including but not limited to polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid, aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues; and naturally occurring or synthetic compositions. An agent can be applied to the media, where it contacts the cell and induces its effects. Alternatively, an agent can be intracellular, e.g. as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected from, for example, unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

In some embodiments, the retinaldehyde increasing agent can be retinaldehyde. In some embodiments, the retinaldehyde increasing agent can be a retinaldehyde precursor, e.g. retinol and/or beta-carotene.

Figure 7:
FIG. 7 depicts a schematic of Rald biosynthesis and degradation.
Figure 8:
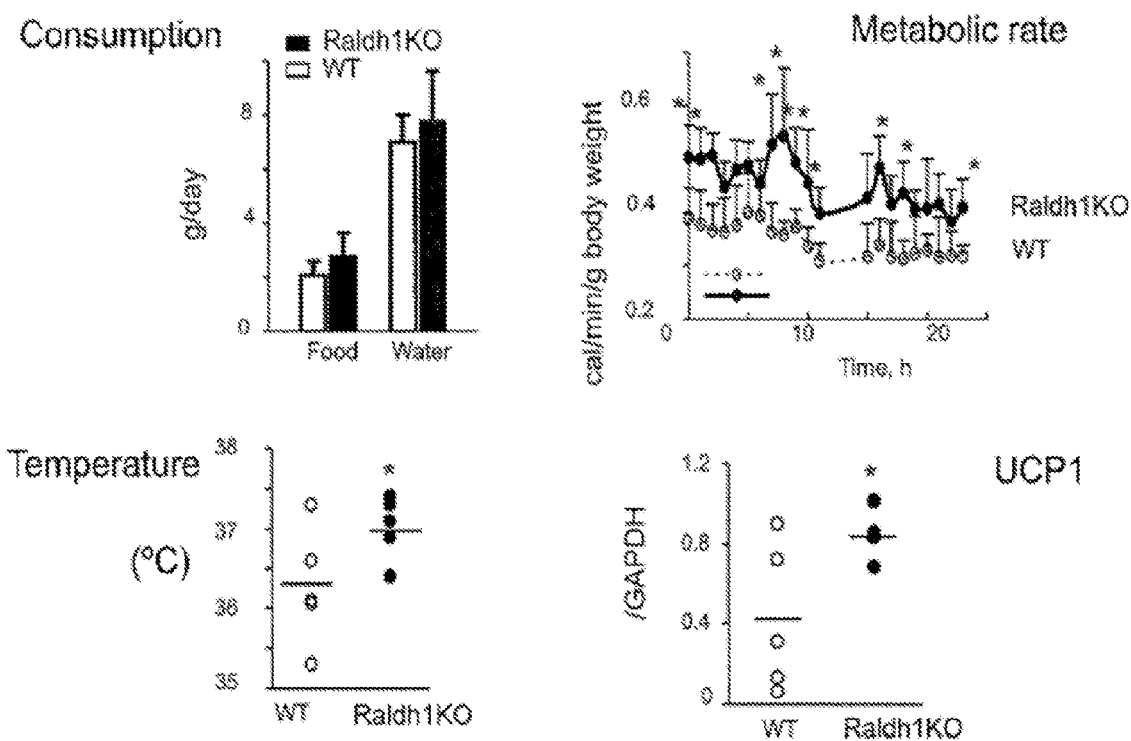
FIG. 8 demonstrates that mice lacking Raldh1 display an increase in energy dissipation. Food and water consumption, metabolic rate, body temperature, and UCP1 expression (normalized to GAPDH expression) is shown in Raldh1 knockout (Raldh1KO) and wildtype mice.
Figure 9:
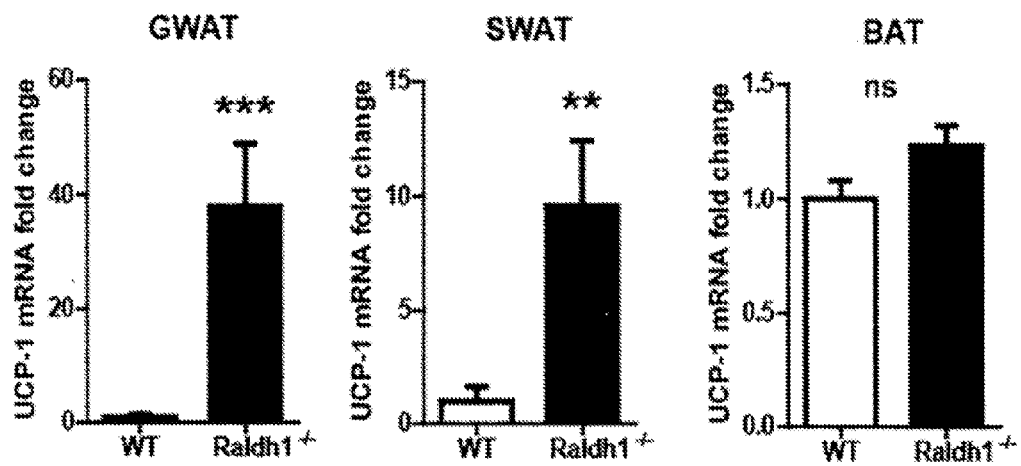
FIG. 9 demonstrates that Raldh1 deficiency induces UCP-1 expression in white adipose tissue (WAT). Fold change of UCP-1 mRNA for Raldh$^{-/-}$ mice relative to wildtype mice is shown for GWAT, SWAT, and BAT.
Figure 10:
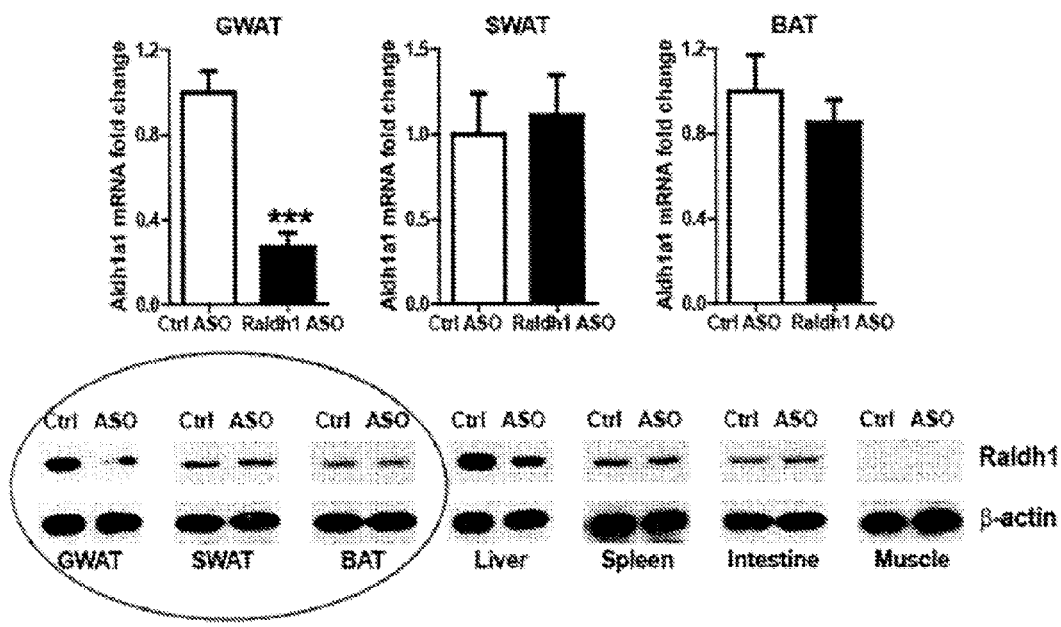
FIG. 10 demonstrates that antisense oligonucleotide (ASO) treatment selectively decreases Raldh1 in visceral WAT. Graphs of the fold change in Aldh1a1 mRNA levels GWAT, SWAT, and BAT and images of protein expression levels in the indicated tissues are depicted.
Figure 11:
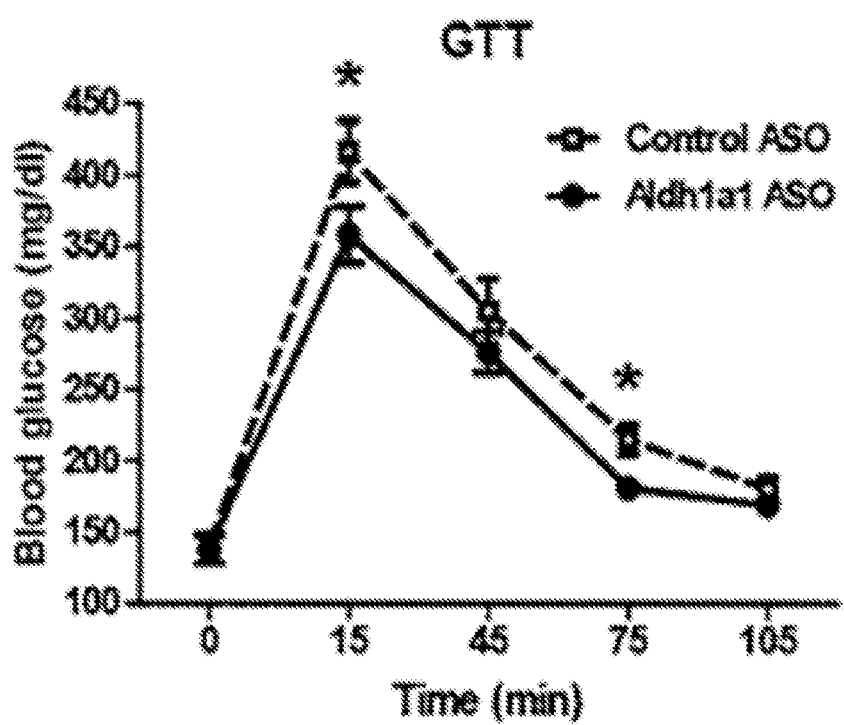
FIG. 11 demonstrates that Raldh1 ASO treatment improves glucose metabolism in established obesity. The results of a glucose tolerance test (GTT) are shown for mice treated with control ASO and Aldh1a1 ASO.

As depicted in FIG. 7 and described in the Examples herein, Aldh1a1 catalyzes the conversion of Rald to retinoic acid. Accordingly, in some embodiments, the retinaldehyde increasing agent can be an inhibitor of Aldh1a1. As used herein, "inhibitor of Aldh1a1" refers to an agent that can decrease the level and/or activity of Aldh1a1. As used herein "Aldh1a1," "aldehyde dehydrogenase 1 family, member A1," or "Raldh", which are used interchangeably, refer to a dehydrogenase that catalyzes the conversion of Rald to retinoic acid and is expressed in WAT. Aldh1a1 is the major post-natal isoform of Aldh1. The sequence of Aldh1a1 polypeptides and nucleic acids encoding Aldh1a1 are known in the art for a number of species, e.g. human Aldh1a1 (polypeptide: SEQ ID NO: 04, NCBI Ref Seq: NP_000680; mRNA: SEQ ID NO: 03, NCBI Ref Seq: NM_000689) (NCBI Gene ID: 216).

The level and/or activity of Aldh1a1 can be measured using methods known in the art. By way of non-limiting example, the level of Aldh1a1 can be measured using RT-PCR with primers specific for Aldh1a1 (see, e.g. the primer pairs provided in Table 1) or by immunochemistry using anti-Aldh1a1 antibodies (e.g. Cat No. ab52492; Abcam; Cambridge, Mass.). Aldh1a1 activity can be determined, e.g. by determining the levels of Rald and retinoic acid present in the cell (e.g. by mass spectroscopy), or by determining the level of a marker of Aldh1a1 activity, e.g. UCP-1 expression (where increased UCP-1 expression indicates a decreased level of Aldh1a1 activity).

In some embodiments, the inhibitor of Aldh1a1 can be specific, e.g. it can inhibit the expression and/or activity of Aldh1a1 but not off-target genes, e.g. other Aldh enzymes (e.g. Aldh2 or Aldh3).

Inhibitors of the expression of a given gene can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of an mRNA transcript of Aldh1a1. The use of these iRNAs enables the targeted degradation of mRNA transcripts of Aldh1a1, resulting in decreased expression and/or activity of Aldh1a1. The following detailed description discloses how to make and use compositions containing iRNAs to inhibit the expression of Aldh1a1, as well as compositions and methods for treating diseases and disorders caused by or modulated by the expression of Aldh1a1, e.g. obesity.

In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the mRNA level found in the cell without the presence of the iRNA.

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the invention relates to a single stranded RNA that promotes the formation of a RISC complex to effect silencing of the target gene.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of Aldh1a1. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, an miRNA is a dsRNA. In another embodiment, a dsRNA is not a naturally occurring miRNA. In another embodiment, an iRNA agent useful to target Aldh1a1 expression is not generated in the target cell by cleavage of a larger dsRNA.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression.

A dsRNA as described herein can further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In one embodiment, at least one end of a dsRNA has a single-stranded nucleotide overhang of 1 to 4, generally 1 or 2 nucleotides. dsRNAs having at least one nucleotide overhang have unexpectedly superior inhibitory properties relative to their blunt-ended counterparts.

In another embodiment, one or more of the nucleotides in the overhang is replaced with a nucleoside thiophosphate. As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

In specific embodiments, the iRNA comprises a single strand comprising the sequence of SEQ ID NO: 01. In some embodiments, the iRNA comprises the sequence of SEQ ID NO: 01. In some embodiments, the iRNA consists of the sequence of SEQ ID NO: 01.

In some embodiments, the one strand of the iRNA comprises and/or consists of the sequence of SEQ ID NO: 01 and the second strand comprises and/or consists of a nucleic acid sequence complementary to the first strand, e.g. at least the portion of the first strand comprising SEQ ID NO: 01. In this aspect, one of the two sequences is complementary to the other of the two sequences, with one of the sequences being substantially complementary to a sequence of a Aldh1a1 mRNA. As such, in this aspect, a dsRNA will include two oligonucleotides, where one oligonucleotide is described as the sense strand and the second oligonucleotide is described as the corresponding antisense strand of the sense strand. As described elsewhere herein and as known in the art, the complementary sequences of a dsRNA can also be contained as self-complementary regions of a single nucleic acid molecule, as opposed to being on separate oligonucleotides.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer RNA duplex structures can be effective as well. In the embodiments described above, dsRNAs described herein can include at least one strand of a length of minimally 21 nt. It can be reasonably expected that shorter duplexes having the sequence of, e.g. SEQ ID NO: 01 minus only a few nucleotides on one or both ends may be similarly effective as compared to the dsRNAs described above. Hence, dsRNAs having a partial sequence of at least 15, 16, 17, 18, 19, 20, or more contiguous nucleotides from, e.g. SEQ ID NO: 01, and differing in their ability to inhibit the expression of Aldh1a1 by not more than 5, 10, 15, 20, 25, or 30% inhibition from a dsRNA comprising the full sequence, are contemplated according to the invention.

Further, it is contemplated that for any iRNA sequence, e.g., SEQ ID NO: 01, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of Alh1a1, the RNA strand generally does not contain any mismatch within the central 13 nucleotides. The methods described herein or methods known in the art can be used to determine whether an iRNA containing a mismatch to a target sequence is effective in inhibiting the expression of Aldh1a1. Consideration of the efficacy of iRNAs with mismatches in inhibiting expression of Aldh1a1 is important, especially if the particular region of complementarity in Alh1a1 is known to have polymorphic sequence variation within the population.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. No. RE39,464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_{.n}OCH_3$, $O(CH_2)_nNH_2$, $O(CH_2)_nCH_3$, $O(CH_2).ONH_2$, and $O(CH_2)_nON[(CH_2).CH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic (PK) modulator. As used herein, a "PK modulator" refers to a pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

For macromolecular drugs and hydrophilic drug molecules, which cannot easily cross bilayer membranes, entrapment in endosomal/lysosomal compartments of the cell is thought to be the biggest hurdle for effective delivery to their site of action. In recent years, a number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. Chem. Biol. 11, 713-723.). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. Polymers Adv. Technol. 13, 992-999; Kakudo, Chaki, T., S. et al. (2004). Transferrin-Modified Liposomes Equipped with a pH-Sensitive Fusogenic Peptide: An Artificial Viral-like Delivery System. Biochemistry 436, 5618-5628; Yessine, M. A. and Leroux, J. C. (2004). Membrane-destabilizing polyanions: interaction with lipid bilayers and endosomal escape of biomacromolecules. Adv. Drug Deliv. Rev. 56, 999-1021; Oliveira, S., van Rooy, I. et al. (2007). Fusogenic peptides enhance endosomal escape improving iRNA-induced silencing of oncogenes. Int. J. Pharm. 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs is described in Biochim. Biophys. Acta 1559, 56-68).

In certain embodiments, the endosomolytic components of the present invention can be polyanionic peptides or peptidomimetics which show pH-dependent membrane activity and/or fusogenicity. A peptidomimetic can be a small protein-like chain designed to mimic a peptide. A peptidomimetic can arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Libraries of compounds can be screened for their differential membrane activity at endosomal pH versus neutral pH using a hemolysis assay. Promising candidates isolated by this method may be used as components of the modular compositions of the invention. A method for identifying an endosomolytic component for use in the compositions and methods of the present invention may comprise: providing a library of compounds; contacting blood cells with the members of the library, wherein the pH of the medium in which the contact occurs is controlled; determining whether the compounds induce differential lysis of blood cells at a low pH (e.g., about pH 5-6) versus neutral pH (e.g., about pH 7-8).

Exemplary endosomolytic components include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component can contain a chemical group (e.g., an amino acid) which will undergo a change in charge or protonation in response to a change in pH. The endosomolytic component may be linear or branched. Exemplary primary sequences of endosomolytic components include H2N-(AALEALAEALEALAEALEA-LAEAAAAGGC)-CO2H (SEQ ID NO: 2); H2N-(AALAEALAEALAEALAEALAEALAAAAGGC)-CO2H (SEQ ID NO: 5); and H2N-(ALEALAEALEALAEA)-CONH2 (SEQ ID NO: 6).

In certain embodiments, more than one endosomolytic component can be incorporated into the iRNA agent of the invention. In some embodiments, this will entail incorporating more than one of the same endosomolytic component into the iRNA agent. In other embodiments, this will entail incorporating two or more different endosomolytic components into iRNA agent.

These endosomolytic components can mediate endosomal escape by, for example, changing conformation at endosomal pH. In certain embodiments, the endosomolytic components can exist in a random coil conformation at neutral pH and rearrange to an amphipathic helix at endosomal pH. As a consequence of this conformational transition, these peptides may insert into the lipid membrane of the endosome, causing leakage of the endosomal contents into the cytoplasm. Because the conformational transition is pH-dependent, the endosomolytic components can display little or no fusogenic activity while circulating in the blood (pH ~7.4). "Fusogenic activity," as used herein, is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

In addition to hemolysis assays, as described herein, suitable endosomolytic components can be tested and identified by a skilled artisan using other methods. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an iRNA agent described herein is constructed using one or more test or putative fusogenic agents. The iRNA agent can be labeled for easy visualization. The ability of the endosomolytic component to promote endosomal escape, once the iRNA agent is taken up by the cell, can be evaluated, e.g., by preparation of an endosome preparation, or by microscopy techniques, which enable visualization of the labeled iRNA agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition. A two-step assay can also be performed, wherein a first assay evaluates the ability of a test compound alone to respond to changes in pH, and a second assay evaluates the ability of a modular composition that includes the test compound to respond to changes in pH.

In one embodiment of the aspects described herein, a ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides suitable for use with the present invention can be a natural peptide, e.g., tat or antennopedia peptide, a synthetic peptide, or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 7). An RFGF analogue (e.g., amino acid sequence AALLPVL-LAAP (SEQ ID NO: 8)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 9)) and the *Drosophila Antennapedia* protein (RQIKIWFQNRRMK-WKK (SEQ ID NO: 10)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In some embodiments, the iRNA oligonucleotides described herein further comprise carbohydrate conjugates. The carbohydrate conjugates are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$). In some embodiments, the carbohydrate conjugate further comprises other ligand such as, but not limited to, PK modulator, endosomolytic ligand, and cell permeation peptide.

In some embodiments, the conjugates described herein can be attached to the iRNA oligonucleotide with various linkers that can be cleavable or non cleavable. The term "linker" or "linking group" means an organic moiety that connects two parts of a compound. Linkers typically comprise a direct bond or an atom such as oxygen or sulfur, a unit such as $NR^8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^8)$, C(O), substituted or unsubstituted aryl, substituted or unsubstituted heteroaryl, substituted or unsubstituted heterocyclic; where $R^8$ is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. Further examples of cleavable linking groups include but are not limited to, redox-cleavable linking groups (e.g. a disulphide linking group (—S—S—)), phosphate-based cleavable linkage groups, ester-based cleavable linking groups, and peptide-based cleavable linking groups. Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds. "Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction may be performed either with the RNA still bound to the solid support or following cleavage of the RNA, in solution phase. Purification of the RNA conjugate by HPLC typically affords the pure conjugate.

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA. Absorption or uptake of an iRNA can occur through unaided diffusive or active cellular processes, or by auxiliary agents or devices. For example, for in vivo delivery, iRNA can be injected into a tissue site or administered systemically. In vivo delivery can also be by a beta-glucan delivery system, such as those described in U.S. Pat. Nos. 5,032,401 and 5,607,677, and U.S. Publication No. 2005/0281781, which are hereby incorporated by reference in their entirety. In vitro introduction into a cell includes methods known in the art such as electroporation and lipofection. Further approaches are described herein below or are known in the art.

In general, any method of delivering a nucleic acid molecule can be adapted for use with an iRNA (see e.g., Akhtar S. and Julian R L. (1992) Trends Cell. Biol. 2(5): 139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, WAT). Local administration to a treatment site maximizes local concentration of the agent, limits the exposure of the agent to systemic tissues that may otherwise be harmed by the agent or that may degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684;

Bitko, V., et al (2005) Nat. Med. 11:50-55). For administering an iRNA systemically for the treatment of a disease or condition (e.g. obesity), the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) Nature 432: 173-178). Conjugation of an iRNA to an aptamer has been shown to inhibit tumor growth and mediate tumor regression in a mouse model of prostate cancer (McNamara, J O., et al (2006) Nat. Biotechnol. 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

In another aspect, iRNA targeting Aldh1a1 can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue.

The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In some embodiments, the iRNA can be delivered via a liposome. As used in the present invention, the term "liposome" means a vesicle composed of amphiphilic lipids arranged in a spherical bilayer or bilayers. A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

In one embodiment, an iRNA featured in the invention is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs are described, e.g., in U.S. Patent Application Publication Nos. 20060240093, 20070135372, and in International Application No. WO 2009082817. These applications are incorporated herein by reference in their entirety.

In some embodiments, the iRNA can be targeted to a desired tissue, e.g. targeted to adipose tissue. Targeted delivery of iRNAs is described, for example in Ikeda and Taira Pharmaceutical Res 2006 23:1631-1640; which is incorporated by reference herein in its entirety. The intravenous delivery of modified siRNAs which are targeted to the liver and fat tissue as been described, e.g. in Soutschek et al., Nature 2004 432:173-8; which is incorporated by reference herein in its entirety. By way of example, the inhibitor can be targeted to adipose tissue by encapsulating the inhibitor in a liposome comprising ligands of receptors expressed on adipose cells, e.g. FABP4. In some embodiments, the liposome can comprise apatamers specific for adipose tissue, see, e.g. Liu et al. PLOS One 2012 7:e37789; which is incorporated by reference herein in its entirety. Further non-limiting examples of ligands that can target the iRNA to an adipose cell include, e.g. fatty acids and glycerol.

As used herein, a variant of a given inhibitory nucleic acid sequence can be a sequence which is at least 90% identical to the reference sequence, e.g. 90% identical, 95% identical, 98% identical, or more identical.

In some embodiments, the inhibitor of Aldh1a1 can be a small molecule inhibitor. Non-limiting examples of small molecule inhibitors of Aldh1a1 can include diethyl aminobenzaldehyde (DEAB) (e.g. a molecule having the structure of Formula I); citral; 4-(n,n-dipropylamino)benzaldehyde (DPAB); ampal; disulfiram; S-methyl-N,N-diethylthiocarbamate sulfoxide (DETC-MeSO); coprine; cyanamide daidzin; 1-aminocyclopropanol (ACP), cephalosporins, gossypol; isosorbide esters; metronidazole; or metabolites or analogs of any of the foregoing exhibiting ALDH1-inhibiting activity. Further non-limiting examples of small molecule inhibitors of Aldh1a1 can include tetraethylthioperoxydicarbonic diamide, bis-diethylthiocarbamoyl disulfide, tetraethylthiuram disulfide, CRONETAL™, ABSTENIL™, STOPETYL™, CONTRAIN™, ANTADIX™, ANIETANOL™, EXHORAN™, ethyl thiurad, ANTABUSE™, ETABUSE™, Ro-Sulfiram, ABSTINYL™, THIURANIDE™, ESPERAL™, TETRADINE™, NOXAL™ TETRAETI™; disulfram analogs (e.g. dithioperoxothioates as described in, e.g. WO/2011/097218); S-methyl N,N-diethyldithiocarbamate; S-methyl N,N-diethylthiocarbamate sulfoxide; (e.g. thiocarbamate sulfoxides are described, e.g in International Patent Publication No. WO/1992/018121); coprine (N5-(i.e. hydroxycyclopropyl)-L-glutamine) as described in, e.g. U.S. Pat. No. 4,076,840; cyanamide and metabolites thereof, e.g. as described in DeMaster et al., Biochem. Biophys. Res. Com. 107:1333-1339 (1982) (e.g. TEMPOSIL™, DIPSANE™ and ABSTEM™, and COLME™, see e.g. U.S. Pat. No. 6,255,497); daidzin and analogs thereof (e.g. daidzein-7-O-[oocarboxynonyl]ether (deczein), daidzein-7-O-[oocarboxyhexyl]ether (hepzein), daidzein-7-O-[oocarboxypentyl]ether (hexzein), daidzein, puerarin, and dicarboxymethyl-daidzein) which are described, e.g. in U.S. Pat. Nos. 5,204,369; 5,886,028; 6,121,010; and 6,255,497; 1-aminocyclopropanol (ACP); cephalosporins; gossypol; isosorbide esters; metronidazole; tryptophan, benserazide and combinations of tryptophan and benserazide (see, e.g. Patent No. EP1294377) or metabolites or analogs of any of the foregoing exhibiting ALDH1-inhibiting activity. All of the foregoing references are incorporated herein by reference in their entireties. Aldh inhibitors have been described in the art, e.g. Koppaka et al. Pharmacological Reviews 2012 64:520-539; which is incorporated by reference herein in its entirety. Aldh1a1 inhibitors are also available commercially, e.g. DEAB (Cat No.; Sigma-Aldrich, St. Louis, Mo.). In some embodiments, one or more Aldh1a1 inhibitors can be administered, e.g. 2 inhibitors, 3 inhibitors, or more inhibitors. Compositions comprising one or more Aldh1a1 inhibitors are known in the art and described, e.g. in International Patent Publication WO/2012/076897 and WO/2012/050597 which are incorporated herein by reference in their entireties.

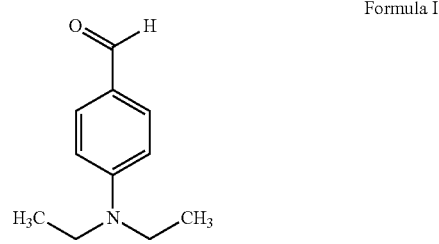

Formula I

In some embodiments, an inhibitor of Aldh1a1 can be an antibody reagent.

In some embodiments, the retinaldehyde increasing agent and/or delivery of the agent can be targeted to a specific cell type, e.g. as described above herein for iRNA agents. In some embodiments, the specific cell type is a WAT cell and/or a visceral WAT cell. In some embodiments, the agent is active or substantially active in certain cell types, e.g. when administered systemically as described elsewhere herein inhibitory nucleic acids comprising SEQ ID NO: 01 decrease Aldh1a1 expression in visceral WAT levels but no effect on expression of Aldh1a1 in subcutaneous WAT is observed.

In some embodiments, both retinaldehyde (or a precursor thereof) and an inhibitor of Aldh1a1 can be administered. In embodiments where multiple retinaldehyde increasing agents are administered, e.g. an inhibitor of Aldh1a1 and retinaldehyde or multiple inhibitors of Aldh1a1, the agents can be administered in any combination with, e.g. concurrently or sequentially. In embodiments where multiple agents are administered, the agents can be administered at varying times and/or for varying durations.

In some embodiments, a subject treated according to the methods described herein can be a subject in need of a reduction of white adipose tissue. A subject in need of reduction of WAT can be a subject that has or has been diagnosed as overweight, obese, or in need of a reduction of WAT and/or body mass. In some embodiments, a subject in need of reduction of WAT can also be a subject in need of reduction of WAT in order to prevent the development and/or slow the progression of an unhealthy BMI, obesity, and/or obesity-related condition. In some embodiments, a subject in need of reduction of WAT can also be a subject in need of reduction of WAT for aesthetic reasons.

In some embodiments, the subject can be a subject in need of treatment for a metabolic disorder. The term "metabolic disorder" refers to any disorder associated with or aggravated by impaired or altered glucose regulation or glycemic control, such as, for example, insulin resistance. Such disorders include, but are not limited to obesity; excess adipose tissue; diabetes; fatty liver disease; non-alcoholic fatty liver disease; metabolic syndrome; dyslipidemia; hypertension; hyperglycemia; and cardiovascular disease. "Metabolic syndrome", which is distinct from metabolic disorder, refers to a combination of medical disorders that, when occurring together, increase the risk of developing cardiovascular disease and diabetes. A number of definitions of metabolic syndrome have been established, e.g by the American Heart Association and the International Diabetes Foundation. As but one example, the WHO defines metabolic syndrome as the presence of any one of diabetes mellitus, impaired glucose tolerance, impaired fasting glucose or insulin resistance and two of the following: blood pressure equal to or greater than 140/90 mmHg, dyslipidemia, central obesity, and microalbuminuria. In some embodiments, the metabolic disorder can be selected from the group consisting of: obesity; excess adipose tissue; diabetes; and cardiovascular disease.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) Am J Clin Nutr 72:694-701.) These BMI ranges are based on the effect of body weight on increased risk for disease. Some common conditions related to high BMI and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI. Furthermore, the BMI threshold that separates normal, overweight, and obese can vary, e.g. with age, gender, ethnicity, fitness, and body type, amongst other factors. In some embodiments, a subject with obesity can be a subject with a body mass index of at least about 25 kg/m$^2$ prior to administration of a treatment as described herein. In some embodiments, a subject with obesity can be a subject with a body mass index of at least about 30 kg/m$^2$ prior to administration of a treatment as described herein.

As used herein "excess adipose tissue" refers to an amount of adipose tissue present in the subject which is more than is desired. In some embodiments, excess adipose tissue can refer to adipose tissue which a medical practitioner has determined is contributing or can contribute to obesity and/or metabolic disease. In some embodiments, excess adipose tissue can refer to adipose tissue which a medical practitioner has determined to be more than the medically-recommended amount of adipose tissue for the particular subject and can be influenced by age, gender, ethnicity, fitness, and body type, amongst other factors. In some embodiments, excess adipose tissue can be adipose tissue that is determined to be more than aesthetically desirable.

As used herein, "diabetes" refers to diabetes mellitus, a metabolic disease characterized by a deficiency or absence of insulin secretion by the pancreas. As used throughout, "diabetes" includes Type 1, Type 2, Type 3, and Type 4 diabetes mellitus unless otherwise specified herein. The onset of diabetes is typically due to a combination of hereditary and environmental causes, resulting in abnormally high blood sugar levels (hyperglycemia). The two most common forms of diabetes are due to either a diminished production of insulin (in type 1), or diminished response by the body to insulin (in type 2 and gestational). Both lead to hyperglycemia, which largely causes the acute signs of diabetes: excessive urine production, resulting compensatory thirst and increased fluid intake, blurred vision, unexplained weight loss, lethargy, and changes in energy metabolism. Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation. In some embodiments, the diabetes can be Type 2 diabetes. Type 2 diabetes (non-insulin-dependent diabetes mellitus (NIDDM), or adult-onset diabetes) is a metabolic disorder that is primarily characterized by insulin resistance (diminished response by the body to insulin), relative insulin deficiency, and hyperglycemia. In some embodiments, a subject can be pre-diabetic, which can be characterized, for example, as having elevated fasting blood sugar or elevated post-prandial blood sugar.

As used herein, "cardiovascular disease" refers to various clinical diseases, disorders or conditions involving the heart, blood vessels or circulation. The diseases, disorders or conditions may be due to atherosclerotic impairment of coronary, cerebral or peripheral arteries. Cardiovascular disease includes, but is not limited to, coronary artery disease, peripheral vascular disease, hypertension, myocardial infarction, heart failure, stroke, and angina.

In one aspect, described herein is a method for inducing weight loss in a subject, the method comprising, administering a therapeutically effective amount of a retinaldehyde increasing agent to the subject; wherein a therapeutically effective amount of a retinaldehyde increasing agent is an amount sufficient to induce a BAT-like phenotype in WAT cells.

As described herein, administration of a retinaldehyde increasing agent causes WAT to assume a BAT-like phenotype, one effect of which is an increase of thermogenesis. As demonstrated herein, the increase of thermogenesis in WAT can cause an increase in body temperature and/or an increased ability to maintain core body temperature. Accordingly, in some embodiments, a subject in need of treatment according to the methods described herein can be a subject selected from the group consisting of: a subject in need of an increased body temperature; a subject in need of treatment or prevention of exposure to low temperatures; and a subject in need of treatment or prevention of hypothermia.

In some embodiments of any of the foregoing aspects, a therapeutically effective amount of a retinaldehyde increasing agent can be an amount that does not substantially reduce lean body mass of the subject.

In some embodiments, the methods described herein relate to treating a subject having or diagnosed as excess body fat and/or obesity with a retinaldehyde increasing agent. Subjects having, e.g. obesity can be identified by a physician using current methods of diagnosis, e.g. BMI index. This can include, but is not limited to, a subject diagnosed as having and/or at risk of having or developing type II diabetes, metabolic syndrome, insulin resistance, cardiac disease, early-onset myocardial infarction, osteoarthritis, gout, heart disease, gall bladder disease, fatty liver disease, sleep apnea, gall stones, and numerous types of cancer. Also envisioned is the treatment of patients who desire treatment for aesthetic reasons (i.e. to maintain a desired weight, BMI, or appearance) even if they are at a healthy weight or BMI prior to treatment. Risk factors which can increase the likelihood of a subject being at risk of having or developing a higher than desired BMI include a high caloric intake, sedentary lifestyle, hypothyroidism and a family history of high BMI or obesity.

In some embodiments, the methods and compositions described herein can relate to the treatment of a human subject. In some embodiments, the methods and compositions described herein can relate to the treatment of a companion animal, e.g. a dog or a cat.

The compositions and methods described herein can be administered to a subject having or diagnosed as having, e.g. obesity. In some embodiments, the methods described herein comprise administering an effective amount of a composition described herein, e.g. a retinaldehyde increasing agent to a subject in order to alleviate a symptom of, e.g. obesity. As used herein, "alleviating a symptom of" a condition is ameliorating any symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection. In some embodiments, the administration can be intraperitoneal, oral, and/or intravenous. Administration can be local or systemic.

The term "effective amount" as used herein refers to the amount of a retinaldehyde increasing agent needed to alleviate at least one or more symptom of the disease or disorder, and relates to a sufficient amount of pharmacological composition to provide the desired effect. The term "therapeutically effective amount" therefore refers to an amount of a retinaldehyde increasing agent that is sufficient to provide a particular, e.g. anti-obesity, effect when administered to a typical subject. An effective amount as used herein, in various contexts, would also include an amount sufficient to delay the development of a symptom of the disease, alter the course of a symptom or disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a retinaldehyde increasing agent which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for thermogenesis, among others. The dosage can be determined by a physician and adjusted, as necessary, to suit observed effects of the treatment.

In some embodiments, the technology described herein relates to a pharmaceutical composition comprising a retinaldehyde increasing agent as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. retinaldehyde increasing agent as described herein.

In some embodiments, the pharmaceutical composition comprising a retinaldehyde increasing agent as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of a retinaldehyde increasing agent as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a retinaldehyde increasing agent as disclosed herein can also be incorporated into the parenteral dosage forms of the disclosure, including conventional and controlled-release parenteral dosage forms.

Certain pharmaceutical compositions comprising a retinaldehyde increasing agent can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the retinaldehyde increasing agent can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In certain embodiments, an effective dose of a composition comprising a retinaldehyde increasing agent as described herein can be administered to a patient once. In certain embodiments, an effective dose of a composition comprising a retinaldehyde increasing agent can be administered to a patient repeatedly. For systemic administration, subjects can be administered a therapeutic amount of a composition comprising a retinaldehyde increasing agent, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. obesity by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the retinaldehyde increasing agent. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising a retinaldehyde increasing agent can be administered over a period of time, such as over a 5 minute, 10 minute, 15 minute, 20 minute, or 25 minute period.

The dosage ranges for the administration of a retinaldehyde increasing agent, according to the methods described herein depend upon, for example, the form of the agent, its potency, and the extent to which symptoms, markers, or indicators of a condition described herein are desired to be reduced, for example the percentage reduction desired for BMI or the extent to which, for example, glucose tolerance are desired to be induced. The dosage should not be so large as to cause adverse side effects, such as unhealthy weight loss or abnormally high body temperatures. Generally, the dosage will vary with the age, condition, and sex of the patient and can be determined by one of skill in the art. The dosage can also be adjusted by the individual physician in the event of any complication.

The efficacy of a retinaldehyde increasing agent in, e.g. the treatment of a condition described herein, or to induce a response as described herein (e.g. weight loss) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. BMI or UCP-1 expression in WAT. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. BMI). It is well within the ability of one skilled in the art to monitor efficacy of administration and/or treatment by measuring any one of such parameters, or any combination of parameters. Efficacy can be assessed in animal models of a condition described herein, for example treatment of a mouse model of diabetes. When using an experimental animal model, efficacy of treatment is evidenced when a statistically significant change in a marker is observed, e.g. UCP-1 expression, metabolic rate, and/or core body temperature.

In vitro and animal model assays are provided herein which allow the assessment of a given dose of a retinaldhyde increasing agent. By way of non-limiting example, the effects of a dose of a retinaldehyde increasing agent can be assessed by determining UCP-1 polypeptide levels. A non-limiting example of a protocol for such an assay is as follows: C3H10T1/2 or MEFs are differentiated in vitro. Briefly, cells are grown to confluence in DMEM, 10% fetal bovine serum (FBS) and 1% penicillin/streptomycin followed by standard adipogenic induction (20 nM insulin, 1 nM T3, 0.5 mM isobutylmethylxanthine, 1 pM dexamethasone, 0.125 mM indomethacin) and stimulation with retinoids, retinoid antagonists or vehicle (DMSO) as indicated. After a 48 h induction phase, growth media can be supplemented with insulin and T3, and changed every other day up to day 6. The differentiated cells are contacted with the retinaldehyde increasing agent and Western blotting is performed with, e.g. anti-UCP-1 antibody (Cat No. 23841; Abcam; St. Louis, Mo.).

The efficacy of a given dosage combination can also be assessed in an animal model, e.g. a mouse model of obesity. For example, the extent to which a retinaldehyde increasing agent improves glucose tolerance can be determined by administering the agent to a mouse. Glucose is then injected intraperitoneally after a 12 hour fast and blood glucose concentrations measured periodically, e.g., up to 120 min by glucometer (Abbott Laboratories, Abbott Park, Ill.).

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on a an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and U.S. Pat. No. 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

A further kind of antibody reagent is an intrabody i.e. an intracellular antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Intrabodies work within the cell and bind intracellular protein. Intrabodies can include whole antibodies or antibody binding fragments thereof, e.g. single Fv, Fab and F(ab)'2, etc. Methods for intrabody production are well known to those of skill in the art, e.g. as described in WO 2002/086096. Antibodies will usually bind with at least a KD of about 1 mM, more usually at least about 300 µM, typically at least about 10 µM, more typically at least about 30 µM, preferably at least about 10 µM, and more preferably at least about 3 µM or better.).

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Avidity is the measure of the strength of binding between an antigen-binding molecule (such as an antibody reagent described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody reagent described herein) will bind to their cognate or specific antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$. Preferably, a binding site on an antibody reagent described herein will bind to the desired antigen with an affinity less than 500 nM, preferably less than 200 nM, more preferably less than 10 nM, such as less than 500 pM. Specific binding of an antibody reagent to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an agent (e.g. an antibody reagent) described herein to bind to a target, such a peptide comprising, e.g. Aldh1a1, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if an agent described herein binds to a first peptide comprising Aldh1a1 or an epitope thereof with a $K_D$ of $10^{-5}$ M or lower, but not to another randomly selected peptide, then the agent is said to specifically bind the first peptide. Specific binding can be influenced by, for example, the affinity and avidity of the agent and the concentration of the agent. The person of ordinary skill in the art can determine appropriate conditions under which an agent selectively bind the targets using any suitable methods, such as titration of an agent in a suitable cell and/or peptide binding assay.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives to hybridoma-based production systems. The main advantages of transgenic animals are potential high yields from renewable sources.

As used herein, an "epitope" can be formed both from contiguous amino acids, or noncontiguous amino acids juxtaposed by folding of a protein. Epitopes formed from contiguous amino acids are typically retained on exposure to denaturing solvents, whereas epitopes formed by folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

Nucleic acid molecules encoding amino acid sequence variants of antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode a monoclonal antibody molecule or antigen binding region thereof. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression may be avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in media rich in glucose can be utilized to obtain recombinant antibodies or antigen-binding portions thereof. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of skill See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those of ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli., for example. Other gene expression elements useful for the expression of cDNA encoding antibodies or antigen-binding portions thereof include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983). Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Nonlimiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled chimeric, humanized, or composite human antibodies, portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, *E. coli* K12 strains such as *E. coli* W3110 (ATCC 27325), *Bacillus* species, enterobacteria such as *Salmonella typhimurium* or *Serratia marcescens*, and various *Pseudomonas* species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

In some embodiments, one or more antibodies or antibody reagents thereof as described herein can be produced in vivo in an animal that has been engineered or transfected with one or more nucleic acid molecules encoding the polypeptides, according to any suitable method.

In some embodiments, an antibody or antibody reagent thereof as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete H₂L₂ antibodies. As discussed above, it is possible to co-express H and L chains in the same cells to achieve intracellular association and linkage of H and L chains into complete tetrameric H₂L₂ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or H₂L₂ molecules via either route could be transfected with plasmids encoding additional copies of peptides, H, L, or H plus L chains in conjunction with additional selectable markers to generate cell lines with enhanced properties, such as higher production of assembled H₂L₂ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. No. 6,080,560; U.S. Pat. No. 6,512,162; WO 0129242. Several plant-derived antibodies have reached advanced stages of development, including clinical trials (see, e.g., Biolex, NC).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, NY, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," *Immunol Rev* 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen," *J Immunol* 148:1149 (1992), which is incorporated herein by reference in its entirety. Alternatively, antibody coding sequences can be incorporated in transgenes for introduction into the genome of a transgenic animal and subsequent expression in the milk of the transgenic animal (e.g., according to methods described in U.S. Pat. No. 5,741,957, U.S. Pat. No. 5,304,489, U.S. Pat. No. 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol. Meth. (Lefkovits & Pernis, eds., Acad. Press, NY, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to Aldh1a1.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10% at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. The decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of obesity. A subject can be male or female.

A subject can be one who has been previously diagnosed with or identified as suffering from or having a condition in need of treatment (e.g. in need of treatment for obesity) or one or more complications related to such a condition, and optionally, have already undergone treatment for obesity or the one or more complications related to obesity. Alternatively, a subject can also be one who has not been previously diagnosed as having obesity or one or more complications related to obesity. For example, a subject can be one who exhibits one or more risk factors for obesity or one or more complications related to obesity or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a translated gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of inhibitory nucleic acids featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of Aldha1a1.

As used herein, "target sequence" refers to a contiguous portion of the nucleotide sequence of an mRNA molecule formed during the transcription of Aldh1a1, including messenger RNA (mRNA) that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all sub-ranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs (bp), while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (an mRNA) refers to a polynucleotide that is substantially complementary to a contiguous portion of the mRNA of interest (e.g., an mRNA encoding Alhd1a1). For example, a polynucleotide is complementary to at least a part of an Aldh1a1 mRNA if the sequence is substantially complementary to a non-interrupted portion of an mRNA encoding Aldh1a1.

The term "double-stranded RNA" or "dsRNA," as used herein, refers to an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. Strictly speaking, a "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one embodiment, modified RNAs contemplated for use in methods and compositions described herein are peptide nucleic acids (PNAs) that have the ability to form the required duplex structure and that permit or mediate the specific degradation of a target RNA via a RISC pathway.

In one aspect, a modified ribonucleoside includes a deoxyribonucleoside. In such an instance, an iRNA agent can comprise one or more deoxynucleosides, including, for example, a deoxynucleoside overhang(s), or one or more deoxynucleosides within the double stranded portion of a dsRNA. However, it is self evident that under no circumstances is a double stranded DNA molecule encompassed by the term "iRNA."

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, the term "RNAi" refers to any type of interfering RNA, including but not limited to RNAi, siRNA, shRNA, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the generation of active cleavage complexes and the site-specific cleavage of mRNA, such sequences can be incorporated into vectors for direct expression or used for direct introduction to cells). The term "RNAi" and "RNA interference" with respect to an agent of the technology described herein, are used interchangeably herein.

As used herein a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA can be formed from separate complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA formed from a single, at least partially self-complementary strand of RNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow. The double-stranded portion that forms upon intramolecular hybridization of the sense and antisense sequences corresponds to the targeted mRNA sequence.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. obesity. The term "treating" includes reducing or alleviating at least one adverse effect or symptom of a condition, disease or disorder associated with obesity. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). In the case of obesity or being overweight, the adverse effect can include not only clinical symptoms or markers of obesity-related disease, but also aesthetic indicators, such that a non-obese, but overweight individual's desire for weight loss or lower BMI is encompassed as a condition. Beneficial or desired clinical results include, but are not limited to, alleviation of one or more symptom(s), decrease in BMI, delay or slowing of the clinical progression of a condition, and amelioration or palliation of a condition.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of inducing a brown adipose tissue (BAT)-like phenotype in a white adipose tissue (WAT) of a subject; the method comprising administering a therapeutically effective amount of a retinaldehyde increasing agent to the subject.
2. The method of paragraph 1, wherein the BAT-like phenotype comprises an increase in a parameter selected from the group consisting of:
    RAR expression; RAR activity; UCP-1 expression; thermogenesis; and uncoupled mitochondrial respiration.
3. The method of any of paragraphs 1-2, wherein the WAT is visceral WAT.
4. The method of any of paragraphs 1-3, wherein the subject is a subject in need of a reduction of white adipose tissue.
5. The method of any of paragraphs 1-4, wherein the subject is a subject in need of treatment for a metabolic disorder.
6. The method of paragraph 5, wherein the metabolic disorder is selected from the group consisting of:
    obesity; excess adipose tissue; diabetes; and cardiovascular disease.
7. The method of paragraph 5, wherein the subject with obesity has a body mass index of at least about 25 $kg/m^2$ prior to administration.
8. The method of paragraph 5, wherein the subject with obesity has a body mass index of at least about 30 $kg/m^2$ prior to administration.
9. The method of any of paragraphs 1-3, wherein the subject is a subject selected from the group consisting of:
    a subject in need of an increased body temperature; a subject in need of treatment or prevention of exposure to low temperatures; and a subject in need of treatment or prevention of hypothermia.
10. A method for inducing weight loss in a subject, the method comprising, administering a therapeutically effective amount of a retinaldehyde increasing agent to the subject;
    wherein a therapeutically effective amount of a retinaldehyde increasing agent is an amount sufficient to induce a BAT-like phenotype in WAT cells.
11. The method of any of paragraphs 1-10, wherein the therapeutically effective amount of a retinaldehyde increasing agent does not substantially reduce lean body mass of the subject.

12. The method of any of paragraphs 1-11, wherein the retinaldehyde increasing agent is retinaldehyde.
13. The method of any of paragraphs 1-11, wherein the retinaldehyde increasing agent is an inhibitor of Aldh1a1.
14. The method of paragraph 13, wherein the inhibitor of Aldh1a1 is an inhibitory nucleic acid.
15. The method of paragraph 14, wherein the inhibitory nucleic acid comprises the sequence of SEQ ID NO:1 or a variant thereof.
16. The method of paragraph 13, wherein the inhibitor of Aldh1a1 is a small molecule inhibitor.
17. The method of paragraph 13, wherein the inhibitor is selected from the group consisting of:
    diethyl aminobenzaldehyde (DEAB); citral; 4-(n,n-dipropylamino)benzaldehyde (DPAB); ampal; disulfiram; S-methyl-N,N-diethylthiocarbamate sulfoxide (DETC-MeSO); coprine; cyanamide daidzin; 1-aminocyclopropanol (ACP), cephalosporins, gossypol; isosorbide esters; metronidazole; or metabolites or analogs of any of the foregoing exhibiting ALDH1-inhibiting activity.
18. The method of any of paragraphs 1-17, wherein both retinaldehyde and an inhibitor of Aldh1a1 are administered.
19. The method of any of paragraphs 1-18, wherein the administration is local.
20. The method of any of paragraphs 1-18, wherein the administration is systemic.
21. The method of paragraph 20, wherein the administration is selected from the group consisting of: intraperitoneal; oral; and intravenous.
22. The method of any of paragraphs 1-21, wherein the subject is human.
23. The method of any of paragraphs 1-21, wherein the subject is a companion animal.
24. The method of paragraph 23, wherein the subject is a dog or cat.
25. The use of a retinaldehyde increasing agent to induce a brown adipose tissue (BAT)-like henotype in a white adipose tissue (WAT) of a subject; wherein a therapeutically effective amount of a retinaldehyde increasing agent is administered to the subject.
26. The use of paragraph 25, wherein the BAT-like phenotype comprises an increase in a parameter selected from the group consisting of:
    RAR expression; RAR activity; UCP-1 expression; thermogenesis; and uncoupled mitochondrial respiration.
27. The use of any of paragraphs 25-26, wherein the WAT is visceral WAT.
28. The use of any of paragraphs 25-27, wherein the subject is a subject in need of a reduction of white adipose tissue.
29. The use of any of paragraphs 25-28, wherein the subject is a subject in need of treatment for a metabolic disorder.
30. The use of paragraph 29, wherein the metabolic disorder is selected from the group consisting of: obesity; excess adipose tissue; diabetes; and cardiovascular disease.
31. The use of paragraph 30, wherein the subject with obesity has a body mass index of at least about 25 $kg/m^2$ prior to administration.
32. The use of paragraph 30, wherein the subject with obesity has a body mass index of at least about 30 $kg/m^2$ prior to administration.
33. The use of any of paragraphs 25-32, wherein the subject is a subject selected from the group consisting of:
    a subject in need of an increased body temperature; a subject in need of treatment or prevention of exposure to low temperatures; and a subject in need of treatment or prevention of hypothermia.
34. The use of a retinaldehyde increasing agent for inducing weight loss in a subject, wherein a therapeutically effective amount of a retinaldehyde increasing agent is administered to the subject; and wherein a therapeutically effective amount of a retinaldehyde increasing agent is an amount sufficient to induce a BAT-like phenotype in WAT cells.
35. The use of any of paragraphs 25-34, wherein the therapeutically effective amount of a retinaldehyde increasing agent does not substantially reduce lean body mass of the subject.
36. The use of any of paragraphs 25-35, wherein the retinaldehyde increasing agent is retinaldehyde.
37. The use of any of paragraphs 25-35, wherein the retinaldehyde increasing agent is an inhibitor of Aldh1a1.
38. The use of paragraph 37, wherein the inhibitor of Aldh1a1 is an inhibitory nucleic acid.
39. The use of paragraph 38, wherein the inhibitory nucleic acid comprises the sequence of SEQ ID NO:1 or a variant thereof.
40. The use of paragraph 37, wherein the inhibitor of Aldh1a1 is a small molecule inhibitor.
41. The use of paragraph 40, wherein the inhibitor is selected from the group consisting of:
    diethyl aminobenzaldehyde (DEAB); citral; 4-(n,n-dipropylamino)benzaldehyde (DPAB); ampal; disulfiram; S-methyl-N,N-diethylthiocarbamate sulfoxide (DETC-MeSO); coprine; cyanamide daidzin; 1-aminocyclopropanol (ACP), cephalosporins, gossypol; isosorbide esters; metronidazole; or metabolites or analogs of any of the foregoing exhibiting ALDH1-inhibiting activity.
42. The use of any of paragraphs 25-41, wherein both retinaldehyde and an inhibitor of Aldh1a1 are administered.
43. The use of any of paragraphs 25-42, wherein the administration is local.
44. The use of any of paragraphs 25-42, wherein the administration is systemic.
45. The use of paragraph 24, wherein the administration is selected from the group consisting of: intraperitoneal; oral; and intravenous.
46. The use of any of paragraphs 25-45, wherein the subject is human.
47. The use of any of paragraphs 25-45, wherein the subject is a companion animal.
48. The use of paragraph 47, wherein the subject is a dog or cat.

EXAMPLES

Example 1

Retinaldehyde Dehydrogenase 1 Regulates a Thermogenic Program in White Adipose Tissue Promoting brown adipose tissue (BAT) formation and function may reduce obesity. Recent data link retinoids to energy balance but a specific role for retinoid metabolism in white versus brown fat is unknown. Retinaldehyde dehydrogenases (Aldhs) are rate-limiting enzymes in converting retinaldehyde (Rald) to retinoic acid. Here we show that Aldh1a1 is expressed predominately in white adipose tissue (WAT) but not BAT. Genetic Aldh1a1 deficiency induced a BAT-like transcriptional program in WAT that drove uncoupled respiration and adaptive thermogenesis. WAT-selective Mc:1MM knockdown conferred this BAT program in obese mice, limiting weight gain and improving glucose homeostasis. Rald, whose endogenous concentrations are elevated in Aldh1a1 deficiency, induced uncoupling protein-1 (UCP-1) in white adipocytes by selectively activating the retinoic acid receptor (RAR), recruiting the co-activator PGC-1a, and inducing UCP-1 promoter activity. These data establish Aldh1a1 and its substrate Rald as novel determinants of adipocyte plasticity and adaptive thermogenesis with potential therapeutic implications.

Obesity is closely associated with many disorders, including atherosclerosis and type 2 diabetes[1,2]. Although excess caloric intake and decreased energy expenditure promote overall weight gain, visceral adiposity is particularly associated with cardiometabolic risk[3]. As such, unique factors may control the development and function of specific fat depots. Whereas white adipose tissue (WAT) stores energy in form of triglycerides, brown adipose tissue (BAT) oxidizes fatty acids and dissipates energy through uncoupled respiration and heat production". WAT is the main adipose depot in humans, however, recent work establishes the presence of BAT in humans and its association with leanness[6,7]. The distinct aspects of adipocyte biology require further understanding and may represent a therapeutic strategy to combat obesity and its complications. Although the presence of brown adipocytes in WAT and factors determining white versus brown adipogenesis have received considerable attention[8-12], the exact origin of white and brown adipocytes and the potential for adipocyte plasticity in terms of white versus brown characteristics remains under debate[13,14].

Retinoids—vitamin A metabolites with diverse, essential biological functions—have recently been linked to the control of adipogenesis and energy homeostasis, with effects on obesity, diabetes and cardiovascular disease[15-19]. Retinoids exert these actions largely by activating the retinoic acid receptor (RAR) and the retinoid X receptor (RXR), nuclear hormone receptors that regulate gene expression[20,21]. Retinoid formation relies on a network of enzymes in which dietary vitamin A, or retinol, is first oxidized to retinaldehyde (Rald) by alcohol and retinal dehydrogenases. Subsequently, retinaldehyde dehydrogenases (Aldhs), also known as aldehyde dehydrogenases, irreversibly convert Rald to retinoic acid (RA)—the rate limiting step of RA formation[20-22].

The inventors have identified Rald as an active signaling metabolite in WAT and an inhibitor of adipogenesis in 3T3-L1 cells[16]. Deficiency in Aldh1a1, the major post-natal Aldh isoform, results in higher Rald concentrations[16,23], and protects mice against diet-induced obesity and diabetes by increasing energy expenditure[16]. However, the mechanisms for this hypermetabolic phenotype, its dependency on high-fat feeding and human relevance remained unclear.

Described herein is a demonstration of Aldh1a1 as a key determinant of WAT plasticity and function involved in regulating white versus brown adipocyte characteristics. In both mice and humans, Aldh1a1 was expressed primarily in visceral WAT and its expression level was highly associated with obesity. In chow-fed mice, Aldh1a1 deficiency dramatically increased both expression of classic BAT markers and uncoupled respiration in WAT, increasing adaptive thermogenesis in viva Rald potently regulated transcription of uncoupling protein-1 (UCP-1) in white adipocytes through effects on RAR and not RXR, including PGC1 a co-activator recruitment. Notably, treating high fat-fed mice with antisense oligonucleotides against Aldh1a1 repressed Aldh1a1 expression selectively in visceral WAT and conferred protection against cold exposure and obesity by inducing a WAT thermogenic program. These findings establish Aldh1a1 and its substrate Rald as novel regulators of white adipose plasticity and adaptive thermogenesis, and identify targeting Aldh1a1 in visceral fat as a novel therapeutic strategy for treating obesity.

Results

Aldh1a1, Predominately Expressed in Visceral Fat, is Associated with Obesity in Mice and Humans.

To consider Aldh1a1's potential role in specific adipose stores, Aldh1a1 mRNA expression and protein levels were analyzed in different fat depots of regular chow-fed C57131/6J mice and metabolically-healthy human subjects of normal weight. In C57BI/6J mice, Aldh1a1 expression was highest in perigonadal white adipose tissue (GWAT), a murine visceral fat depot, significantly lower in inguinal subcutaneous white adipose tissue (SWAT), and barely detectable in interscapular brown adipose tissue (BAT); Aldh1a1 protein levels followed a similar pattern (FIG. 1A). In humans, both Aldh1a1 mRNA and protein were robustly present in visceral adipose tissue (visc AT), with significantly lower levels in abdominal subcutaneous adipose tissue (sc AT, FIG. 1B).

Given that visceral adiposity is strongly implicated in the pathogenesis of obesity-related metabolic disorders, whether adipose Aldh1a1 expression varied with obesity was determined. Aldh1a1 expression was significantly higher in GWAT and visc AT of both high fat-fed C57B1/6J mice and morbidly obese human subjects, respectively, compared to lean controls (FIGS. 1C-1D). Moreover, regression analysis revealed a positive association between Aldh1a1 mRNA expression in visc AT and body mass index ($r^2$=0.39, p<0.001) in 40 human subjects (FIG. 1E). These results implicate Aldh1a1 in visceral adiposity and indicate its association with obesity.

Aldh1a1 Deficiency Induces a Classic Brown Fat Transcriptional Program in White Adipose Tissue.

Figure 2A:
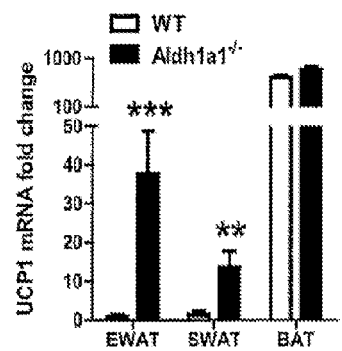
FIGS. 2A-2C demonstrate that Aldh1a1 deficiency is characterized by increased transcription of brown fat markers in white fat.
Figure 2B:
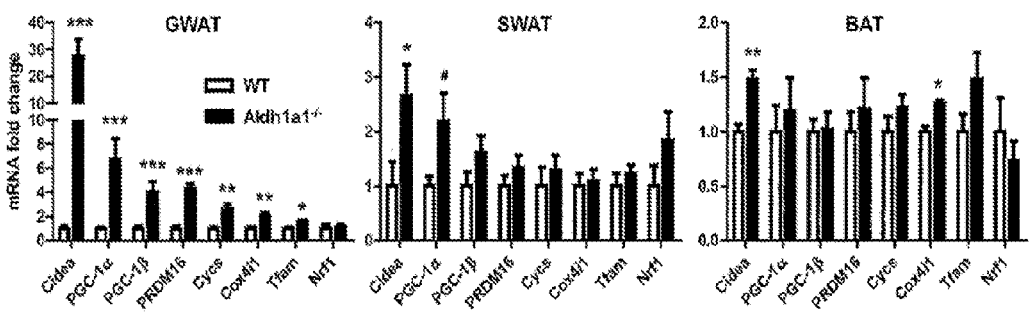
Figure 2C:
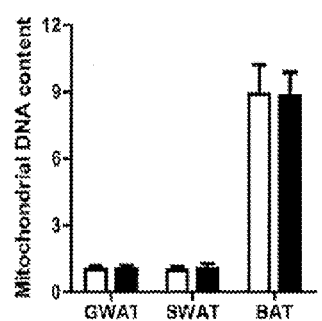

Given this association of Aldh1a1 with obesity (FIGS. 1A-1E) and the enhanced energy expenditure in high fat-fed Aldh1a1-deficient (Aldh1a1") mice[16], mitochondrial uncoupling in WAT and BAT was investigated as a mechanism for energy dissipation in Aldh1a1 deficiency. UCP-1 mRNA (40-fold) and protein expression were significantly induced in GWAT of normal chow-fed Aldh1a1$^{-/-}$ mice versus C57BI/6J wild-type (WT) controls, but significantly less so in SWAT, and remained unchanged in BAT (FIG. 2A). In immunohistochemical studies, lipid droplet size and adipocyte morphology appeared unaltered in Aldh1a1-deficient WAT while UCP-1 was strongly induced, all as compared to WT adipose tissue (data not shown). To further characterize fat in the presence or absence of Aldh1a1, mRNA expression of known BAT markers including cell death activator (Cidea), peroxisome proliferator gamma coactivtor-la and 3 (PGC-la, (3), PR domain containing 16 (PRDM16), cytochrome c (Cycs), cytochrome c oxidase subunit 4i1 (Cox4i1), transcription factor A (Tfam), and nuclear respiratory factor 1 (Nrfl) was measured in GWAT, SWAT, BAT from chow-fed WT and Aldh1a1"" mice. All BAT marker genes were significantly increased in Aldh1a1-deficient GWAT, with Nrfl being the only exception. In contrast, this same gene panel was either unchanged or only modestly increased in SWAT and BAT of Aldh1a1⁻/⁻ versus WT mice (FIG. 2B). It was next tested if altered mitochondrial biogenesis might explain this increase in BAT marker expression in white fat. In GWAT, SWAT, and BAT, mitochondrial DNA content was unchanged between genotypes (FIG. 2C). Electron microscopy in GWAT revealed no differences in mitochondrial density or ultrastructure (data not shown). These data indicate that Aldh1a1 deficiency increases BAT marker expression in visceral WAT without altering mitochondrial biogenesis.

Aldh1a1 Deficiency Activates a Thermogenic Program in White Adipose Tissue.

Figures 3A, 3B, 3C, 3D:
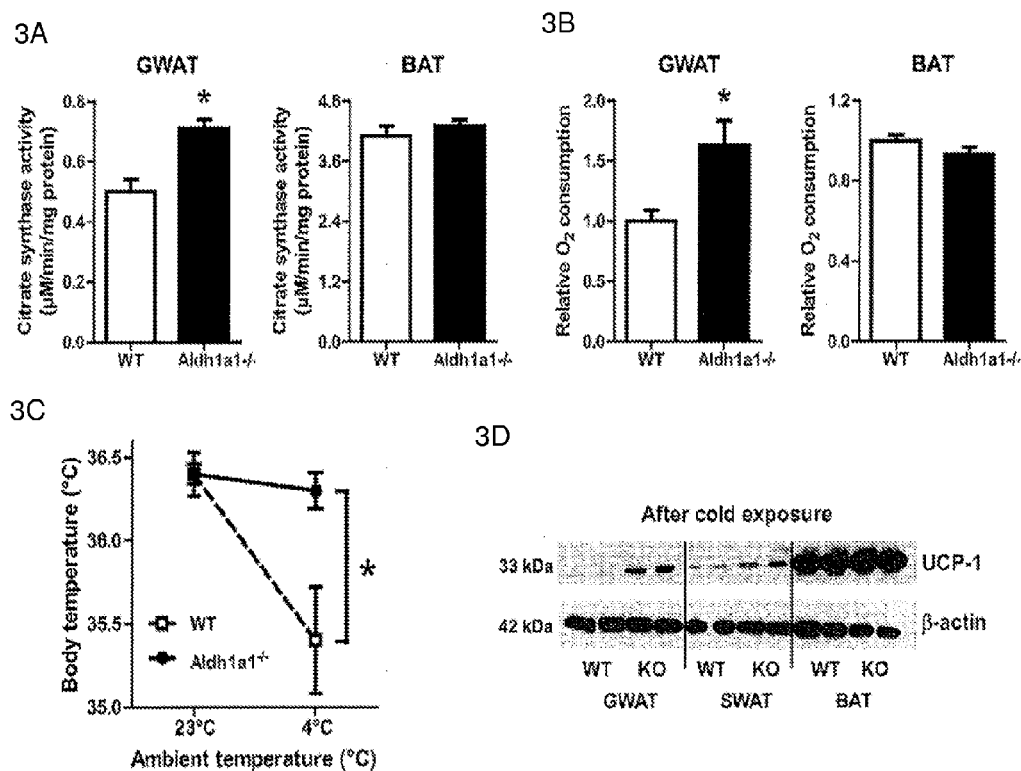
FIGS. 3A-3D demonstrate that Aldh1a1 deficiency activates a thermogenic program in white fat.

To test whether increased UCP-1 expression in GWAT from Aldh1a1⁻/⁻ mice altered GWAT function, mitochondrial activity was assayed using citrate synthase activity, the rate-limiting step of the tricarboxylic acid cycle[24,26]. Citrate synthase activity was significantly increased in GWAT but not BAT from Aldh1a1⁻/⁻ versus WT mice (FIG. 3A). Increased mitochondrial uncoupling drives oxidative phosphorylation, enhancing cellular respiration[4]. Oxygen consumption rates were increased significantly in Aldh1a1-deficient GWAT (1.7-fold) but not BAT (FIG. 3B). Since uncoupled respiration dissipates energy through heat production, core body temperature in WT versus Aldh1a1⁻/⁻ mice was measured at room temperature (23° C.) and during 48 h cold exposure (4° C.). At 23° C., body temperature did not differ between genotypes. At 4° C., WT mice body temperatures dropped significantly; in striking contrast, mice lacking Aldh1a1 were completely protected against cold exposure (FIG. 3C). Consistent with these findings, cold exposure markedly increased UCP-1 expression in Aldh1a1-deficient GWAT and to a minor extent in SWAT, with no evidence for genotypic differences in BAT (FIGS. 3D-3E). Cold exposure induced emergence of BAT-like UCP1-positive multilocular adipocytes in Aldh1a1-deficient WAT (FIG. 3E). These results argue for a role of Aldh1a1 in regulating uncoupled respiration and adaptive thermogenesis through effects in WAT but not BAT.

Rald Promotes UCP-1 Transcription in White Adipocytes.

Figures 4A, 4B, 4C, 4D, 4E, 4F, 4G:
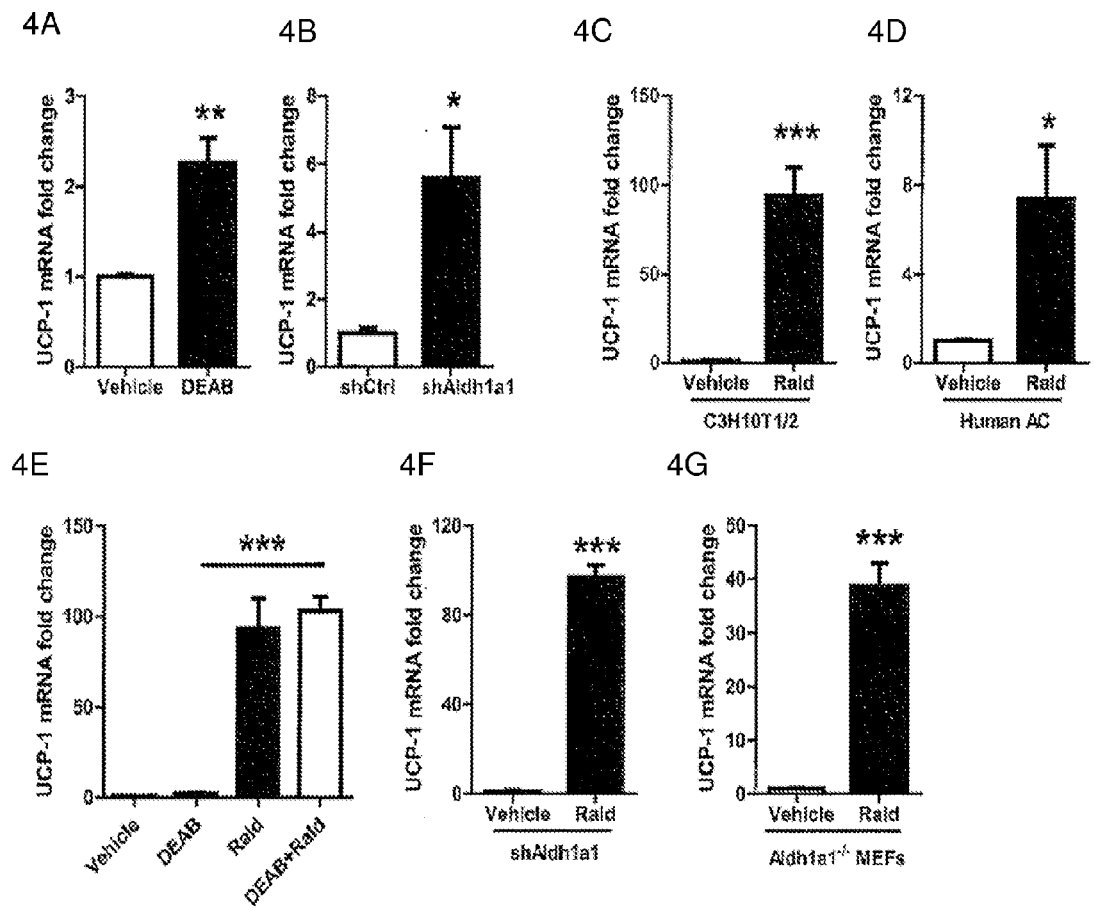
FIGS. 4A-4G demonstrate that Rald induces UCP-1 expression in white adipocytes.

To investigate mechanisms for increased uncoupling in GWAT, chemical and targeted genetic approaches were employed in murine and human adipocyte models. The C3H10T1/2 (10T1/2) cell-line is an established model of adipogenesis[26]. In undifferentiated 10T1/2 cells, Aldh1a1 is not present but is robustly induced during adipogenesis (data not shown). Stimulation of 10T1/2 cells with the Aldh inhibitor diethyl aminobenzaldehyde (DEAB, 1 pM)[27] during adipogenic differentiation significantly increased UCP-1 gene expression as compared to vehicle-treated cells (FIG. 4A). Likewise, stable Aldh1a1 mRNA repression in 10T1/2 cells using shRNA-expressing lentivirus (shAldh1a1, 80% knockdown without compensatory increase in Aldh1a2 or Aldh1a3, data not shown) induced UCP-1 mRNA 5-fold as compared to lentiviral-treated control cells (shCtrl, FIG. 4B). Given that Aldh1a1 deficiency increases endogenous Rald concentrations[16,23], Rald was tested as a UCP-1 transcriptional regulator. Stimulation of 10T1/2 cells with all trans-Retinal (Rald, 1 pM) during adipogenic differentiation induced expression of UCP-1 (100-fold) and other BAT markers including PGC-1β, PRDM16, and Cidea, whereas expression of the adipogenic gene aP2 remained unaltered (FIG. 4C, data not shown). Similarly, Rald stimulation significantly increased UCP-1 expression in differentiating human stromal-vascular cells from subcutaneous fat biopsies (FIG. 4D).

To test if Rald conversion to RA accounted for the increased UCP-1 expression seen above, Rald effects were studied in three distinct in vitro models in which Aldh1a1 expression or function was repressed or absent. Co-stimulation with Rald and the Aldh inhibitor DEAB increased UCP-1 expression to the same extent as Rald alone in differentiating 10T1/2 cells (FIG. 4E). Rald stimulation in shAldh1a1-treated 10T1/2 cells increased UCP-1 mRNA expression 100-fold (FIG. 4F), an effect similar to Raid stimulation of untransfected 10T1/2 cells (FIG. 4C). Finally, Rald stimulation (24 h) in Aldh1a1⁻/⁻ mouse embryonic fibroblast (MEF)-derived adipocytes increased UCP-1 gene expression 40-fold versus vehicle-treated cells. Together these findings support Raid induction of UCP-1 expression in white adipocytes independent of its conversion to RA.

Raid Regulates UCP-1 Expression Through RAR Activation and PGC-1α Co-Activator Recruitment.

Figures 5A, 5B, 5C, 5D, 5E, 5F, 5G, 5H, 5I, 5J:
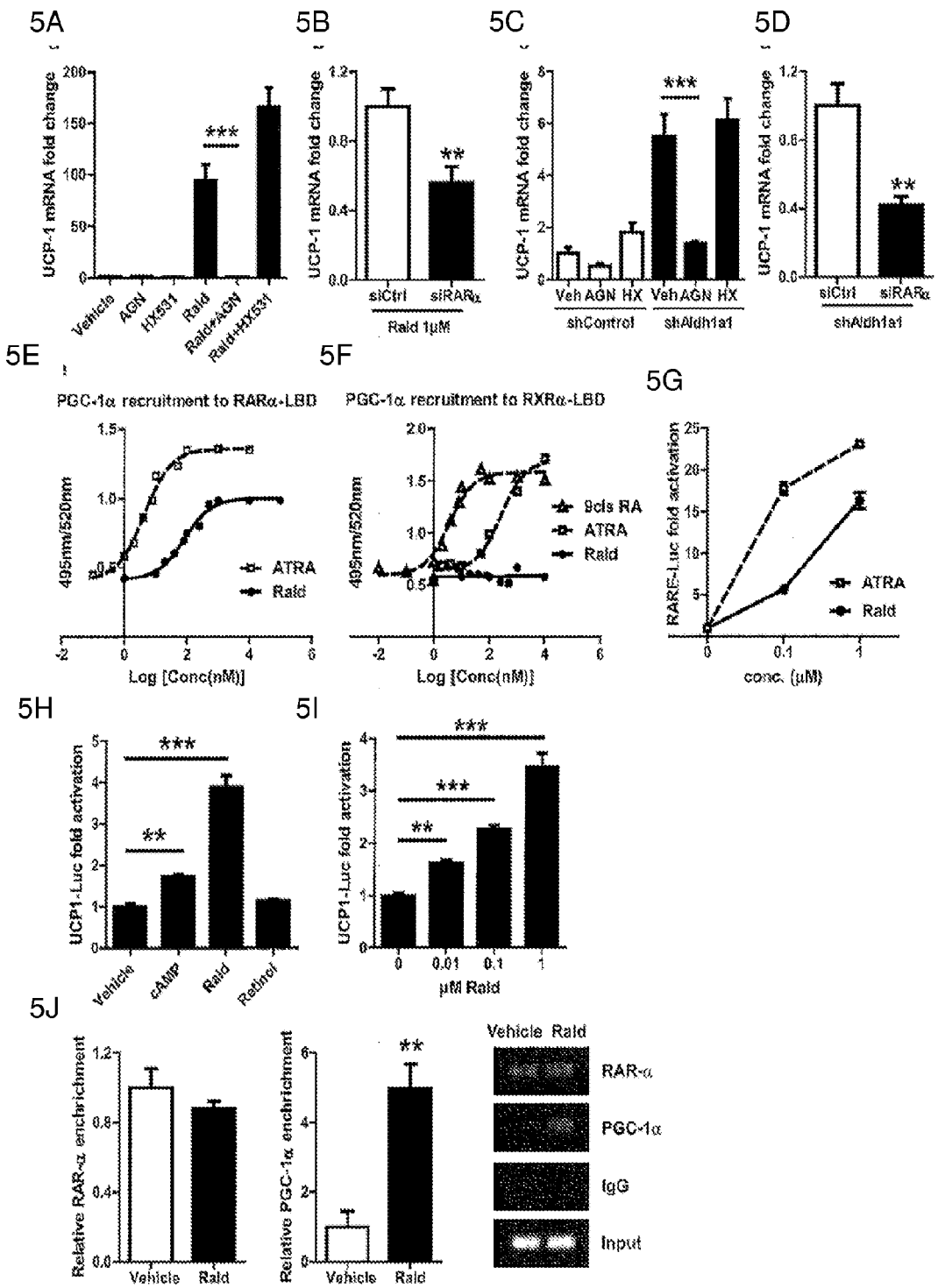
FIGS. 5A-5J demonstrate that Rald mediated UCP-1 expression is RAR-dependent and involves PGC-1a recruitment.

Since retinoids regulate gene expression through retinoid receptor modulation, retinoid receptor involvement in Rald effects on UCP-1 expression was next investigated. Differentiating 10T1/2 cells were stimulated with Rald in the presence or absence of known antagonists to either RAR (AGN193109) or RXR (HX531)[28,29]. While the RAR antagonist AGN193109 completely inhibited Rald-mediated UCP-1 expression, HX531 did not alter UCP-1 expression (FIG. 5A). Importantly, HX531 did significantly inhibit 9cisRA-induced expression of the RA target gene Cyp26a1, verifying HX5131 as a functional RXR antagonist in this experimental model (data not shown). To further consider RAR dependency through an alternate approach, 10T1/2 experiments were repeated in the presence of a validated siRNA to RARα, the major isoform expressed in these cells (data not shown), or control siRNA (siCtrl). RARα mRNA repression in 10T1/2 cells (60%, data not shown) significantly blunted Rald-mediated UCP-1 induction versus siCtrl (FIG. 5B). RXRα siRNA inhibited adipogenesis, resulting in extremely low UCP-1 expression in all treatment groups (data not shown). Similar experiments in shAldh1a1-transfected 10T1/2 cells also demonstrated that increased UCP-1 expression was RAR- but not RXR-dependent (FIGS. 5C-5D).

Raid interaction with RAR was next examined as a potential mechanism for increased UCP1 expression. PGC-1α is a transcriptional co-activator that induces UCP1 expression[30]. Using cell-free time-resolved fluorescence resonance energy transfer (TR-FRET) assays, Rald-mediated recruitment of PGC-1α to either the RARα or RXRα ligand binding domain (LBD) was tested. As expected, in response to their known natural ligands, all-trans RA (ATRA) and 9cisRA potently recruited PGC-1α to RARα and RXRα, respectively. However, Rald alone also effectively recruited PGC-1α to RARα ($EC_{50}$ 82 nM) but had virtually no effect on PGC-1α recruitment to RXRα in these cell-free assays that lack the ability to convert Rald to RA (FIGS. 5E-5F). Stimulation with either ATRA or Rald significantly increased activity of a canonical retinoic acid response element (RARE) luciferase reporter in a concentration-dependent manner (FIG. 5G).

Since the UCP-1 promoter contains several RARE consensus sites[31], whether Rald can directly activate an RARE-containing UCP-1 promoter transfected into undifferentiated 10T1/2 cells, which lack retinoid-converting enzymes, was examined. Stimulation with cAMP (250 uM), a known UCP-1 transcriptional activator[31] significantly increased UCP-1 reporter activity. Notably, Rald, but not its precursor retinol, increased luciferase activity in a concentration-dependent manner (FIGS. 5H-5I). Next, chromatin immunoprecipitation (ChIP) was used to study Rald-dependent transcription factor recruitment to the UCP-1 promoter region in 10T1/2 cells. A robust RARα signal was present at the UCP-1 promoter under basal conditions that did not increase further after Rald stimulation (FIG. 5J). The TR-FRET data above suggested that Rald may recruit PGC-1α to RARα already present on the UCP-1 promoter. Indeed, similar ChIP studies demonstrated that Rald stimulation enriched PGC-1α occupancy at the UCP-1 promoter region 5-fold. Taken together, these data indicate that Rald recruits PGC-1α to RARα at the UCP-1 promoter, thus inducing UCP-1 transcription.

GWAT-Selective Aldh1a1 Knockdown Induces Adaptive Thermogenesis and Limits Progression of Established Obesity.

Figures 6A, 6B, 6C, 6D, 6E, 6F, 6G, 6H, 6I:
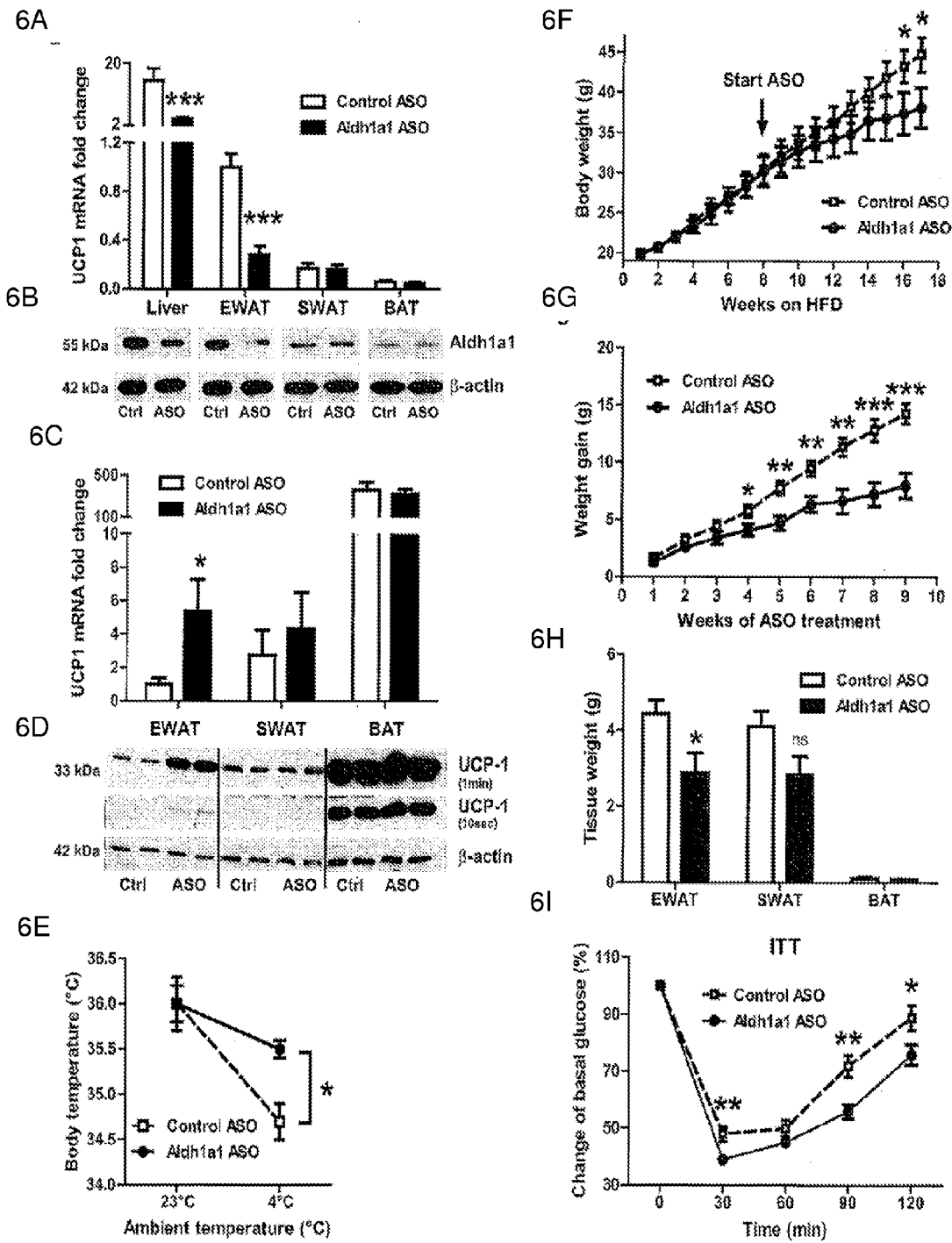
FIGS. 6A-6I demonstrate that ASO-mediated Aldh1a1 knockdown in GWAT promotes white fat thermogenesis and limits diet-induced obesity. C5761/6J mice on standard chow diet were injected intraperitoneally (i.p.) with Aldh1a1 (Aldh1a1 ASO) and control antisense oligonucleotides (Ctrl ASO) for 6 weeks (2 doses of 35 mg/kg/week, n=8/group).

To test if acute, tissue-selective loss of Aldh1a1 in vivo alters UCP1 expression, thermogenesis, and body weight, a validated Aldh1a1 antisense oligonucleotide (Aldh1a1 ASO) or a control ASO (Ctrl ASO) was injected into normal chow-fed C57Bl/6J mice twice a week for 6 weeks (intraperitoneal, 35 mg/kg/dose). The Aldh1a1 ASO treatment significantly decreased Aldh1a1 mRNA and protein levels selectively in liver and GWAT; Aldh1a1 expression remained unchanged in SWAT, BAT, spleen, intestine, and skeletal muscle, compared to Ctrl ASO (FIGS. 6A-6B and data not shown). Aldh1a1 ASO treatment significantly increased UCP-1 expression in GWAT but not SWAT or BAT (FIGS. 6C-6D). To test the functional impact of these effects, core body temperature was measured under ambient and cold-induced conditions. Core body temperature did not differ between Aldh1a1 and Ctrl ASO-treated mice at ambient temperature (23° C.). Exposure to 4° C. (48 h) decreased body temperature in Ctrl ASO-treated mice; in contrast, Aldh1a1 ASO-treated mice were protected significantly against cold exposure (FIG. 6E). To test if GWAT-selective Aldh1a1 repression could modulate established obesity, C57Bl/6J mice were fed a high-fat diet (HFD) for 8 weeks before undergoing Aldh1a1 ASO treatment and continued HFD for an additional 9 weeks. Aldh1a1 ASO treatment significantly limited weight gain in obese mice and decreased GWAT mass (FIG. 6F-6H), resulting in improved insulin and glucose tolerance (FIG. 6I), all as compared to a control ASO. These data reveal that selective Aldh1a1 repression in visceral fat confers induction of a thermogenic program that inhibits body weight gain and improves glucose homeostasis in obesity.

Discussion

Understanding determinants of energy storage and utilization is critical for addressing the epidemic of obesity and its complications. Energy dissipation through uncoupled respiration and increased thermogenesis is a key component of energy metabolism, especially given recent evidence for BAT in humans and its inverse correlation with obesity'. As described herein, promoting BAT or BAT-like characteristics is a therapeutic strategy for treating excess adiposity[32].

Retinoids, and the enzymes that control retinoid formation, represent a complex, highly-regulated system that controls fundamental biological processes, including fuel metabolism[15,17,21]. Mice lacking Aldh1a1, the rate-limiting enzyme in Rald conversion to RA, display enhanced energy expenditure on high fat diet[18], suggesting altered BAT activity. As described herein, Aldh1a1 expression in chow-fed mice displays an adipose depot-specific pattern, lowest in BAT and highest in visceral WAT (FIGS. 1A-1E). Moreover, genetic Aldh1a1 deficiency increased expression of UCP-1 and other classical BAT markers in murine GWAT, with minimal changes in SWAT and BAT (FIGS. 2A-2C). Aldh1a1 deficiency increased mitochondrial enzyme activity and oxygen consumption in GWAT, but not BAT, consistent with increased thermogenic capacity in white fat. Indeed, Aldh1a1$^{-/-}$ mice were completely resistant to cold exposure, establishing Aldh1a1 as a central regulator of WAT thermogenesis independent of BAT changes (FIGS. 3A-3E).

Previous reports found brown-like transformation of white fat predominately in subcutaneous fat, with the visceral depot considered less susceptible to acquiring BAT characteristics[34,35]. In GWAT of Aldh1a1$^{-/-}$ mice, the abundance of UCP1-expressing unilocular white adipocytes under basal conditions (FIG. 2B) and the increased presence of multilocular brown adipocytes after cold exposure (FIG. 3E) indicate that Aldh1a1 deficiency fosters thermogenic activation in visceral fat. This latent thermogenic potential of Aldh1a1-deficient visceral fat is unmasked in response to cold (FIGS. 3A-3E) or high-fat feeding (FIGS. 6A-6I). As described herein, altered retinoid metabolism can promote functional plasticity of adipocytes and identifies Aldh1a1 as a novel determinant of white versus brown fat transformation. Without wishing to be bound by theory, this selective action of Aldh1a1 in GWAT most likely derives from the distinct expression pattern of this enzyme in different fat depots (FIGS. 1A-1B).

Without wishing to be bound by theory, the effect of Aldh1a1 deficiency on white versus brown characteristics in adipocyte appears to involve Rald's action as a transcriptional mediator modulating retinoid receptor activity. Lack of Aldh1a1 is an established model of elevated endogenous Rald concentrations, especially in tissues with high Aldh1a1 expression, such as WAT[16,23]. Rald can inhibit PPARγ/RXR heterodimer formation, impairing adipogenesis in 3T3-L1 cells[16]. Rald is demonstrated herein as a positive transcriptional regulator of UCP-1 in murine and human white adipocytes through RAR-, but not RXR-dependent mechanisms (FIGS. 4A-G and 5A-5J). Rald recruited the co-activator PGC-1α to the UCP-1 promoter in white adipocytes (FIG. 5J), a seminal event in BAT activation[30]. Previously, RA has been shown to activate UCP-1 transcription[31,36]. The observation that Rald's effects on UCP-1 transcription were similar in the presence or absence of the Rald-converting enzyme Aldh1a1 supports Rald itself, and not its conversion to RA, as the relevant mediator in this model (FIGS. 4A-4G and 5A-5J). In contrast to Rald, retinol failed to induce UCP-1 promoter activity (FIG. 5H). The fact that both retinol and Rald can bind to RAR in ligand displacement assays[37], but only Rald activates UCP-1 expression in these experimental models argues for Rald-specific functional effects in WAT.

The impact of an Aldh1a1 ASO on body weight control and glucose metabolism in obese mice (FIGS. 6A-6I) identifies Aldh1a1 as a therapeutic target. GWAT-selective loss of Aldh1a1 through ASO treatment also indicates that specifically targeting visceral fat depots to induce BAT-like characteristics and thermogenesis can have benefits on obesity and glucose homeostasis (FIGS. 6A-6I).

Taken together, it is established herein that Aldh1a1 and its substrate Rald are novel determinants of functional plasticity in WAT, which can activate a thermogenic program that promotes energy dissipation and protection against obesity. Disruption of Aldh1a1 expression or function in visceral fat provides opportunities in targeting and treating specific adipose depots and the complications associated with obesity.

Materials and Methods

Animals and Aldh1a1 Antisense Oligonucleotide.

Aldh1a1-deficient (Aldh1a1$^{4m}$) mice were backcrossed to a C57BL/6J background (>20 generations). Mice were kept on a standard chow diet with a Vitamin A content of 15 IU/g or on high-fat diet (60% kcal fat, Research Diets, New Brunswick, N.J.) as indicated. Mice had free access to food and water except as indicated under Harvard Medical School Institutional Animal Care and Use Committee guidelines. Experiments were conducted using 12-14 week old female mice unless otherwise indicated.

An ASO targeting murine Aldh1a1 and a control ASO not hybridizing to any known murine RNA sequences were synthesized and purified by Isis Pharmaceuticals Inc. (Carlsbad, Calif.) as described previously[39]. In vitro characterization including knockdown validation of the Aldh1a1 ASO was done in murine primary hepatocytes. ASOs (70 mg/kg/wk) were administered via intraperitoneal (i.p.) injection twice weekly.

Human Adipose Tissue Samples.

Paired samples of visceral (omental) and subcutaneous adipose tissue were obtained from Caucasian men (n=8) and women (n=32). Morbidly obese patients (BMI=53.0±0.55 kg/m$^2$, n=20) undergoing laparoscopic gastric banding were matched by age and sex to lean control subjects (BMI=25.2±0.15 kg/m$^2$, n=20) undergoing laparoscopic cholecystectomy or fundoplication. Adipose tissue samples were taken from similar locations in all patients. After excision, tissue specimens were washed in saline buffer, visible blood vessels excised, and immediately snap frozen in liquid nitrogen. Subjects with any infectious, inflammatory, neoplastic or systemic disease, diabetes or other uncontrolled endocrine disease, or receiving antibiotics, anti-inflammatory or anti-obesity drugs were excluded. The study was approved by Medical University of Vienna Ethics Committee. All subjects provided written informed consent.

Body Temperature Measurements.

Core body temperature was assessed in mice as before[49, 41]. WT and Aldh1a1$^{-/-}$ mice (12 week old, n=6/group) were anesthetized (Ketamine/Xylazine/Acepromazine, 100/10/3 mg/kg i.p.) and a telemetric temperature probe (E-mitter, MiniMitter, Bend, Oreg.) was implanted intra-abdominally. One week after surgery, mice were single-housed in open-circuit Oxymax chambers as part of the *Comprehensive Lab Animal Monitoring System* (CLAMS; Columbus Instruments, Columbus, Ohio)[42]. Oxymax chambers were kept in a temperature enclosure with 12 h light/dark cycles at 23° C. and mice had ad-libitum access to food and water. After a 48 h acclimatization phase, core body temperature was recorded every 10 min for 48 h at ambient temperature (23° C.), followed by 48 h cold stimulation (4° C.). After sacrifice, fat depots were dissected and analyzed.

Glucose and Insulin Tolerance Tests.

Glucose (GTT) and insulin tolerance tests (ITT) were performed on mice after fasting (12 h and 6 h, respectively). Mice were injected i.p. either with D-glucose (Sigma, 0.75 g/kg body weight) or recombinant human regular insulin (0.5 U/kg body weight, Humulin R, Eli Lilly, Indianapolis, Ind.); blood glucose concentrations were measured periodically up to 120 min by glucometer (Abbott Laboratories, Abbott Park, Ill.).

Cell Culture Reagents.

Except as noted, media were purchased from Invitrogen (Carlsbad, Calif.), retinolds and other chemicals from Sigma (St. Louis, Mo.). RAR antagonist AGN193109 was obtained from Santa Cruz Biotechnology (Santa Cruz, Calif.).

Isolation of Human Adipose Tissue Stromal-Vascular Fraction and Mouse Embryonic Fibroblasts (MEFs).

Abdominal subcutaneous fat biopsies were obtained from a 22 yrs old female subject undergoing gastric bypass surgery who gave written informed consent. Fat biopsies were immediately washed with phosphate buffered saline (PBS), minced, and digested (1 mg/mi collagenase, 45 min, 37° C.) in DMEM containing 1% BSA. Digested tissues were filtered through sterile 150 pm nylon mesh and centrifuged (250 g, 5 min). The floating fractions containing adipocytes were discarded and he stromal-vascular fraction pellet was resuspended in erythrocyte lysis buffer (154 mM NH4CI, 10 mM KHCO3, 0.1 mM EDTA, 10 min) to remove red blood cells. The cells were further centrifuged at 500 g for 5 min, plated on a 24-well culture dish and grown, and differentiated to mature adipocytes as described below. MEFs were isolated from Aldh1a1$^{-/-}$ embryos at embryonic day 14.5 using standard tech niques[43].

In Vitro Adipocyte Differentiation

C3H10T1/2, isolated human stromal-vascular cells and Aldh1a1$^{-/-}$ MEFs were cultured and differentiated as previously described[8]. Briefly, cells were grown to confluence in DMEM, 10% fetal bovine serum (FBS) and 1% penicillin/streptomycin followed by standard adipogenic induction (20 nM insulin, 1 nM T3, 0.5 mM isobutylmethylxanthine, 1 pM dexamethasone, 0.125 mM indomethacin) and stimulation with retinoids, retinoid antagonists or vehicle (DMSO) as indicated. After a 48 h induction phase, growth media was supplemented with insulin, T3, and indicated retinoids which were changed every other day up to day 6.

Cell Transfection, Reporter Assays, siRNA and Lentivirus Infection.

Undifferentiated C3H10T1/2 cells (which do not express Aldhs) were transfected using Fugene HID (Roche, Basel, Switzerland) in a 24 well plate with pGL3-RARE (Addgene, Cambridge, Mass.) or UCP-1 promoter luciferase reporter constructs as previously described[44]. 24 h after transfection, cells were stimulated with retinoids or cAMP as indicated. Cell lysates were harvested 48 h post transfection and luciferase activity quantified by standard luminometer assay and normalized to 3-galactosidase.

Mission® shRNA constructs targeting Aldh1a1 and a non-targeting control shRNA were purchased from Sigma. To generate lentivirus particles, shRNA constructs were transfected into HEK293TN cells (SA Biosciences, Frederick, Md.) along with the packaging vectors psPAX and pM2DG. After 72 h, virus-containing supernatant was precipitated using polyethylene glycol (SA Biosciences) and concentrated in PBS (30×). For stable cell line generation, C3H10T1/2 cells were infected with lentivirus and selected with puromycin (5 pg/ml) over a 2 week period. For transient knockdown, C3H10T1/2 and shAldh1a1 cells were transfected with siRNA constructs against RARa and RXRa (Ambion, Carlsbad, Calif.) using siDeliverX reagent (Panomics, Santa Clara, Calif.) following manufacturer's protocol. Knockdown was confirmed by mRNA and protein expression.

Chromatin Immunoprecipitation (ChIP).

ChIP was performed in Rald versus vehicle stimulated C3H10T1/2 adipocytes using EZ-Magna ChIP™ kit following manufacturer's instructions (Millipore, Billerica, Mass.) and RARa, PGC-1a, or rabbit lgG antibodies as a negative control (all Santa Cruz). lmmunoprecipitated DNA was amplified by real-time PCR using primers specific for the mouse UCP-1 promoter region. Relative PGC-la and RARa occupancy at the UCP-1 promoter was determined normalized to input DNA Reverse Transcription and Gene Expression.

Total RNA was extracted (RNeasy, Qiagen, Hi[den, Germany), DNase-treated (Qiagen), and reverse-transcribed to cDNA. Gene expression, normalized to 36B4, was analyzed by quantitative real-time RT-PCR (Sybr Green, 96 well plates) using a MyiQ cycler (Bio-Rad, Hercules, Calif.). Primer sequences are available upon request.

Mitochondrial DNA Content.

Genomic DNA was isolated from GWAT, SWAT, and BAT of WT and Aldh1a1$^{-/-}$ mice (n=8/group) using DNeasy Blood & Tissue Kit (Qiagen, Hilden, Germany) following manufacturer's instructions. Quantitative real-time PCR assessed genomic expression of mitochondrial NADH dehydrogenase subunit 1 (ND1) normalized to β-globin.

Immunoblotting.

Homogenized tissue was lysed in RIPA buffer (Boston Bioproducts, Ashland, Mass.) containing protease and phosphatase inhibitors. Standard Western blotting was performed using rabbit polyclonal antibody against UCP-1, rabbit monoclonal antibody against Aldh1a1 (both Abcam, Cambridge, UK), GAPDH and f3-Tubulin (both Santa Cruz Biotechnology). Proteins were detected by chemiluminescence (GE HealthCare Amersham, Amersham, UK).

Immunohistochemistry.

Paraffin sections were prepared from murine GWAT, SWAT and BAT after fixation (10% neutral-buffered formalin). Sections were stained with rabbit polyclonal antibody against UCP-1 (Abcam) and biotinylated secondary goat anti-rabbit antibody (Vector Laboratories Inc., Burlingame, Calif.). Control staining was performed on selected sections with isotype control. Micrographs of stained sections were taken with an Olympus Q-color 3 digital camera attached to an Olympus BX50 microscope (Olympus, Center Valley, Pa.).

Electron Microscopy.

GWAT from WT and Aldh1a1$^{-/-}$ mice (n=4/group) was fixed in 4% formaldehyde, 5% glutaraldehyde in 100 mM phosphate buffer, pH 7.2, for 12 h at 4° C. Ultra-thin sections were cut and micrographs generated with a transmission electron microscope (JEOL, Peabody, Mass.).

Adipose Tissue Citrate Synthase Activity.

GWAT and BAT from WT and Aldh1a1$^{-/-}$ mice (n=6/group) were homogenized in protein extraction buffer (50 mM Tris-HCl, 250 mM Mannitol, 100 mM NaCl, 1 mM EDTA, 1 mM EGTA, 1 mM DTT, 10% Glycerol, 1% Triton, protease inhibitors) to obtain protein lysates. After centrifugation and lipid layer removal, protein concentration was determined using BCA Protein Assay (Thermo Fisher Scientific Inc., Rockford, Ill.). 8 pg protein lysate was used for the citrate synthase activity assay following the manufacturer's protocol (Sigma).

Adipose Tissue Oxygen Consumption.

Oxygen consumption rate (OCR) was determined in mouse adipose tissue using a modified protocol[45]. Briefly, freshly isolated GWAT and BAT from WT and Aldh1a1$^{-/-}$ mice (n=5/genotype) were rinsed with unbuffered KHB media containing NaCl 111 mM, 4.7 mM KCl, MgSO4 2 mM, Na2HPO4 1.2 mM, carnitin 0.5 mM, glucose 2.5 mM. Adipose tissue was cut into small pieces, rinsed with KHB media, and 10 mg tissue placed in each well of a XF24-well Islet Flux plate (Seahorse Bioscience, North Billerica, Mass.). 450 p1 KHB media was added to each well and samples analyzed in the XF24 Extracellular Flux Analyzer (Seahorse Bioscience) at 37° C.[46]. The XF24 Analyzer mixed the media in each well 3×2 min prior to measurements to allow oxygen partial pressure to equilibrate. Basal OCR was measured simultaneously in all wells three times. Five tissue replicates from five mice/genotype were analysed in independent experiments and results normalized to tissue protein content.

Time-Resolved Fluorescence Energy Transfer (TR-FRET).

Lanthascreen" TR-FRET RARa and RXR13 coactivator assays (Invitrogen) were performed as per manufacturer protocol using a PerkinElmer (Waltham, Mass.) EnVision™ fluorescence plate reader. Briefly, a glutathione-S-transferase (GST)-tagged recombinant RARa or RXR!3 ligand binding domain (LBD) was incubated with a terbium-labeled anti-GST antibody and a fluorescein-labeled coactivator peptide (PGC-1a) and increasing concentrations of given retinoids. Binding of exogenous agonist (retinoids) to the LBD causes a conformational change that increases the affinity of the nuclear receptor (RARa or RXR(3) for the coactivator peptide (PGC-1a). The close proximity of the fluorescently labeled coactivator peptide to the terbium-labeled antibody enhances the TR-FRET signal measured by the emission ratio of 520 nm/495 nm.

Statistics.

All data are given as means±SEM. Comparisons between two groups were assessed by unpaired 2-tail Student's t-test after normal distribution was confirmed. Linear regression analysis was performed to evaluate association between Aldh1a1 mRNA expression in human fat and BMI. A p-value of 0.05 or less was considered statistically significant.

REFERENCES

1. Mensah, G. A., et al. Obesity, metabolic syndrome, and type 2 diabetes: emerging epidemics and their cardiovascular implications. *Cardiology clinics* 22, 485-504 (2004).
2. Bray, G. A. & Bell!anger, T. Epidemiology, trends, and morbidities of obesity and the metabolic syndrome. *Endocrine* 29, 109-117 (2006).
3. Klein, S., et al. Waist circumference and cardiometabolic risk: a consensus statement from shaping America's health: Association for Weight Management and Obesity Prevention; NAASO, the Obesity Society; the American Society for Nutrition; and the American Diabetes Association. *Diabetes care* 30, 1647-1652 (2007).
4. Cannon, B. & Nedergaard, J. Brown adipose tissue: function and physiological significance. *Physiological reviews* 84, 277-359 (2004).
5. Farmer, S. R. Molecular determinants of brown adipocyte formation and function. *Genes & development* 22, 1269-1275 (2008).
6. Seale, P., Kajimura, S. & Spiegelman, B. M. Transcriptional control of brown adipocyte development and physiological function—of mice and men. *Genes & development* 23, 788-797 (2009).
7. Cypess, A. M., et al. Identification and importance of brown adipose tissue in adult humans. *The New England journal of medicine* 360, 1509-1517 (2009).
8. Tseng, Y. H., et al. New role of bone morphogenetic protein 7 in brown adipogenesis and energy expenditure. *Nature* 454, 1000-1004 (2008).
9. Seale, P., et al. PRDM16 controls a brown fat/skeletal muscle switch. *Nature* 454, 961-967 (2008).
10. Vegiopoulos, A., et al. Cyclooxygenase-2 controls energy homeostasis in mice by de novo recruitment of brown adipocytes. *Science* 328, 1158-1161 (2010).
11. Hansen, J. B., et al. Retinoblastoma protein functions as a molecular switch determining white versus brown adipocyte differentiation. *Proc Natl Acad Sci USA* 101, 4112-4117 (2004).

12. Fang, S., et al. Corepressor SMRT promotes oxidative phosphorylation in adipose tissue and protects against diet-induced obesity and insulin resistance. *Proc Nail Acad Sci USA* 108, 3412-3417 (2011).
13. Cinti, S. Between brown and white: novel aspects of adipocyte differentiation. *Annals of medicine* 43, 104-115 (2011).
14. Park, K. W., Halperin, D. S. & Tontonoz, P. Before they were fat: adipocyte progenitors. *Cell metabolism* 8, 454-457 (2008).
15. Schwarz, E. J., Reginato, M. J., Shao, D., Krakow, S. L. & Lazar, M. A. Retinoic acid blocks adipogenesis by inhibiting C/EBPbeta-mediated transcription. *Ma! Cell Bic!* 17, 1552-1561 (1997).
16. Ziouzenkova, 0., et al. Retinaldehyde represses adipogenesis and diet-induced obesity. *Nat Med* 13, 695-702 (2007).
17. Kane, M. A., et at. Crbpl Modulates Glucose Homeostasis and Pancreas 9-cis-Retinoic Acid Concentrations. *Mel Cell* 00131, 3277-3285 (2010).
18. Altucci, L., Leibowitz, M. D., Ogilvie, K. M., de Lera, A. R. & Gronemeyer, H. RAR and RXR modulation in cancer and metabolic disease. *Nat Rev Drug Discov* 6, 793-810 (2007).
19. Villarroya, F., Iglesias, R. & Giralt, M. Retinoids and retinoid receptors in the control of energy balance: novel pharmacological strategies in obesity and diabetes. *Curr Med Chem* 11, 795-805 (2004).
20. Ross, A. C. Overview of retinoid metabolism. *J Nutr* 123, 346-350 (1993).
21. Ziouzenkova, 0. & Plutzky, J. Retinoid metabolism and nuclear receptor responses: New insights into coordinated regulation of the PPAR-RXR complex. *FESS Lett* 582, 32-38 (2008).
22. Duester, G., Mic, F. A. & Molotkov, A. Cytosolic retinoid dehydrogenases govern ubiquitous metabolism of retinol to retinaldehyde followed by tissue-specific metabolism to retinoic acid. *Chem Blot Interact* 143.144, 201-210 (2003).
23. Molotkov, A. & Duester, G. Genetic evidence that retinaldehyde dehydrogenase Raldh1 (Aldh1a1) functions downstream of alcohol dehydrogenase Adhl in metabolism of retinol to retinoic acid. *J Biol Chem* 278, 36085-36090 (2003).
24. Wiegand, G. & Remington, S. J. Citrate synthase: structure, control, and mechanism. *Annual review of biophysics and biophysical chemistry* 15, 97-117 (1986).
25. Trounce, I. A., Kim, Y. L., Jun, A. S. & Wallace, D. C. Assessment of mitochondrial oxidative phosphorylation in patient muscle biopsies, lymphoblasts, and transmitochondrial cell lines. *Methods in enzymology* 264, 484-509 (1996).
26. Tang, Q. Q., Otto, T. C. & Lane, M. D. Commitment of C3H10T1/2 pluripotent stem cells to the adipocyte lineage. *Proc Nat! Acad Sci USA* 101, 9607-9611 (2004).
27. Chute, J. P., et al. Inhibition of aldehyde dehydrogenase and retinoid signaling induces the expansion of human hematopoietic stem cells. *Proc Natl Acad Sc! USA* 103, 11707-11712 (2006).
28. Johnson, A. T., Wang, L., Gillett, S. J. & Chandraratna, R. A. High affinity retinoic acid receptor antagonists: analogs of AGN 193109. *Bloorganic & medicinal chemistry letters* 9, 573-576 (1999).
29. Takahashi, B., et al. Novel retinoid X receptor antagonists: specific inhibition of retinoid synergism in RXR-RAR heterodimer actions. *J Med Chem* 45, 3327-3330 (2002).
30. Puigserver, P., et al. A cold-inducible coactivator of nuclear receptors linked to adaptive thermogenesis. *Cell* 92, 829-839 (1998).
31. Alvarez, R., et al. A novel regulatory pathway of brown fat thermogenesis. Retinoic acid is a transcriptional activator of the mitochondria! uncoupling protein gene. *J Biol Chem* 270, 5666-5673 (1995).
32. Cypess, A. M. & Kahn, C. R. Brown fat as a therapy for obesity and diabetes. *Current opinion in endocrinology, diabetes, and obesity* 17, 143-149 (2010).
33. Langin, D. Recruitment of brown fat and conversion of white into brown adipocytes: strategies to fight the metabolic complications of obesity? *Biochimica et biophysica acta* 1801, 372-376 (2010).
34. Guerra, C., Koza, R. A., Yamashita, H., Walsh, K. & Kozak, L. P. Emergence of brown adipocytes in white fat in mice is under genetic control. Effects on body weight and adiposity. *J Clin Invest* 102, 412-420 (1998).
35. Seale, P., et al. Prdml 6 determines the thermogenic program of subcutaneous white adipose tissue in mice. *J Clin Invest* 121, 96-105 (2011).
36. Silva, J. E. & Rabelo, R. Regulation of the uncoupling protein gene expression. *European journal of endocrinology/European Federation of Endocrine Societies* 136, 251-264 (1997).
37. Repa, J. J., Hanson, K. K. & Clagett-Dame, M. All-trans-retinol is a ligand for the retinoic acid receptors. *Proc Nat! Acad Sci USA* 90, 7293-7297 (1993).
38. Crooke, S. T. Progress in antisense technology. *Annual review of medicine* 55, 61-95 (2004).
39. Baker, B. F., et al. 2'-O-(2-Methoxy)ethyl-modified anti-intercellular adhesion molecule 1 (ICAM-1) oligonucleotides selectively increase the ICAM-1 mRNA level and inhibit formation of the ICAM-1 translation initiation complex in human umbilical vein endothelial cells. *J Biol Chem* 272, 11994-12000 (1997).
40. Wernstedt, 1., et al. Reduced stress- and cold-induced increase in energy expenditure in interleukin-6-deficient mice. *American journal of physiology. Regulatory, integrative and comparative physiology* 291, R551-557 (2006).
41. Hodges, M. R., et al. Defects in breathing and thermoregulation in mice with near-complete absence of central serotonin neurons. *The Journal of neuroscience: the official journal of the Society for Neuroscience* 28, 2495-2505 (2008).
42. Kennedy, A. R., et al. A high-fat, ketogenic diet induces a unique metabolic state in mice. *Am J Physiol Endocrinol Metab* 292, E1724-1739 (2007).
43. Xu, J. Preparation, culture, and immortalization of mouse embryonic fibroblasts. *Current protocols in molecular biology/edited by Frederick M. Ausubel [ef al.]* Chapter 28, Unit 28 21 (2005).
44. Brown, J. D., Oligino, E., Rader, D. J., Saghatelian, A. & Plutzky, J. VLDL hydrolysis by hepatic lipase regulates PPARdelta transcriptional responses. *PioS one* 6, e21209 (2011).
45. Yehuda-Shnaidman, E., Buehrer, B., Pi, J., Kumar, N. & Collins, S. Acute stimulation of white adipocyte respiration by PKA-induced lipolysis. *Diabetes* 59, 2474-2483 (2010).
46. Wu, M., et al. Multiparameter metabolic analysis reveals a close link between attenuated mitochondria' bioenergetic function and enhanced glycolysis dependency in

Example 2

Retinaldehyde dehydrogenase 1 determines a thermogenic program in white adipose tissue.

Two functionally distinct types of fat are present in mammals: white adipose tissue (WAT), the primary site of triglyceride storage, and brown adipose tissue (BAT), which promotes energy dissipation through adaptive thermogenesis. Factors that determine white versus brown fat differentiation and function remain poorly understood. Recent data links vitamin A and its retinoid metabolites to the regulation of adipogenesis and energy balance. Retinoid metabolism is tightly controlled by an enzymatic network in which retinaldehyde dehydrogenases (Aldhs) are the rate-limiting enzymes converting retinaldehyde (Rald) to retinoic acid. Previously, it was demonstrated that lack of the Aldh isoform 1a1 protected mice from diet-induced obesity by inducing a hypermetabolic state. However, the mechanism for this phenotype remained unclear.

It is demonstrated herein that Aldh1a1 is predominately expressed in white but not brown fat. Genetic Aldh1a1 deficiency resulted in increased expression of classic BAT markers in WAT of standard chow-fed mice. Moreover, Aldh1a1-deficient mice manifested increased mitochondrial enzyme activity and oxygen consumption in WAT and were resistant to cold exposure as compared to controls. Using antisense approaches, WAT-selective Aldh1a1 knockdown inhibited weight gain in high fat-fed obese mice by inducing expression of a similar thermogenic program. In investigating mechanisms for this effect, it was found that Rald, whose endogenous concentrations are elevated in Aldh1a1 deficiency, is a transcriptional regulator of uncoupling protein 1 (UCP1), the key mediator of adaptive thermogenesis. Rald stimulation in white adipocytes increased UCP1 expression 100-fold in a retinoic acid receptor (RAR) but not retinoic X receptor (RXR)-dependent manner. Rald selectively bound and activated RAR but not RXR, induced UCP1 promoter activity, and recruited the co-activator PGC-1α to the UCP1 promoter.

These data establish Aldh1a1 and Rald as novel determinants of adipocyte function and adaptive thermogenesis in white adipose tissue and point towards a central role of retinoid metabolism in the regulation of energy balance.

Example 3

ALDH1A-1 antisense compound:

Sequence: AACACGACTATGCTGGTTAC (SEQ ID NO: 01)

Extinction Coefficient: 197.68 mM-1×cm-1 @ 260 nm
Molecular Weight: 6920.95 daltons. Cells can be dosed at 5-300 nM using 9 ug/ml Lipofectin to observe robust target inhibition after 0/N incubation. Other cationic lipid formulations can also be used successfully.

Example 4

Promoting brown fat function may counteract obesity through energy dissipation[1]. Retinoids (Vitamin A derivatives) recently linked to energy balance and adipogenesis[2]. Rate limiting step of retinoid formation: Conversion of retinaldehyde (Rald) to retinoic acid (RA) through retinaldehyde dehydrogenases (Raldhs, Aldhs)[2]. Genetic Aldh1a1 deficiency raises endogenous Rald concentrations, protects mice against diet-induced obesity and increases metabolic rate[2,3]. Mechanism has been unclear, increased brown fat activity?

Aldh1a1 expression is highest in visceral white and lowest in brown adipose tissue. Aldh1a1 deficiency activates a brown fat program in visceral white adipose tissue. The Aldh1a1 substrate Rald induces UCP-1 transcription in adipocytes through RAR activation and PGC-1α recruitment. Aldh1a1 antisense oligonucleotide treatment represses Aldh1a1 expression selectively in visceral fat and limits obesity progression by inducing a thermogenic program. Targeting Aldh1a1 in visceral fat represents a novel therapeutic strategy in treating obesity and its metabolic sequelae.

Raldh1 is predominantly expressed in visceral fat, as opposed to fat generally. Raldh1 and its substrate Rald are demonstrated herein to determine brown fat function and thermogenesis in visceral WAT through, at least in part, regulation of UCP-1. WAT-selective Raldh1 knockdown by ASO treatment mitigates obesity and improves metabolic health.

REFERENCES

1) Cypess, A. M., et al. Identification and importance of brown adipose tissue in adult humans. The New England journal of medicine 360, 1509-1517 (2009).

2) Ziouzenkova, O. & Plutzky, J. Retinoid metabolism and nuclear receptor responses: New insights into coordinated regulation of the PPAR-RXR complex. FEBS Lett 582, 32-38 (2008).

3) Molotkov, A. & Duester, G. Genetic evidence that retinaldehyde dehydrogenase Raldh1 (Aldh1a1) functions downstream of alcohol dehydrogenase Adh1 in metabolism of retinol to retinoic acid. J Biol Chem 278, 36085-36090 (2003).

TABLE 1 qRT-PCR primers for Raldh1

| Identity | Sequence | SEQ ID NO |
|---|---|---|
| Human Raldh1 5' | CGTGGCGTACTATGGATGC | 11 |
| Human Raldh1 3' (pair gives an 81 bp product) | GCAGCAGACGATCTCTTTCG | 12 |
| mouse Raldh1 5' | CCATGGATGCTTCAGAGAGG | 13 |
| Mouse Raldh1 3' (pair gives an 106 bp product) | ACTTTCCCACCATTGAGTGC | 14 |

What is claimed herein is:

1. A method of inducing a brown adipose tissue (BAT)-like phenotype in a white adipose tissue (WAT) of a subject; the method comprising administering a therapeutically effective amount of a retinaldehyde increasing agent to the subject wherein the retinaldehyde increasing agent is an inhibitory nucleic acid comprising the sequence of SEQ ID NO:1.

2. The method of claim 1, wherein the BAT-like phenotype comprises an increase in a parameter selected from the group consisting of:
RAR expression; RAR activity; UCP-1 expression; thermogenesis; and uncoupled mitochondrial respiration.

3. The method of claim 1, wherein the WAT is visceral WAT.

4. The method of claim 1, wherein the subject is a subject in need of a reduction of white adipose tissue.

5. The method of claim 1, wherein the subject is a subject in need of treatment for a metabolic disorder.

6. The method of claim 5, wherein the metabolic disorder is selected from the group consisting of:
obesity; excess adipose tissue; diabetes; and cardiovascular disease.

7. The method of claim 6, wherein the subject with obesity has a body mass index of at least about 25 kg/m$^2$ prior to administration.

8. The method of claim 6, wherein the subject with obesity has a body mass index of at least about 30 kg/m$^2$ prior to administration.

9. The method of claim 1, wherein the subject is a subject selected from the group consisting of:
a subject in need of an increased body temperature; a subject in need of treatment of exposure to low temperatures; a subject in need of prevention of injury caused by exposure to low temperatures; and a subject in need of treatment or prevention of hypothermia.

10. The method of claim 1, wherein the therapeutically effective amount of a retinaldehyde increasing agent does not substantially reduce lean body mass of the subject.

11. The method of claim 1, wherein the subject is further administered retinaldehyde.

12. The method of claim 1, wherein the subject is further administered a small molecule inhibitor of Aldh1a1.

13. The method of claim 12, wherein the inhibitor is selected from the group consisting of:
diethyl aminobenzaldehyde (DEAB); citral; 4-(n,n-dipropylamino)benzaldehyde (DPAB); ampal; disulfiram; S-methyl-N,N-diethylthiocarbamate sulfoxide (DETC-MeSO); coprine; cyanamide daidzin; 1-aminocyclopropanol (ACP), cephalosporins, gossypol; isosorbide esters; metronidazole; or metabolites or analogs of any of the foregoing exhibiting ALDH1-inhibiting activity.

14. The method of claim 1, wherein the administration is local.

15. The method of claim 1, wherein the administration is systemic.

16. The method of 15, wherein the administration is selected from the group consisting of:
intraperitoneal; oral; and intravenous.

17. The method of claim 1, wherein the subject is human.

18. The method of claim 1, wherein the subject is a companion animal.

19. The method of claim 18, wherein the subject is a dog or cat.

* * * * *